(12) United States Patent
Boon et al.

(10) Patent No.: US 12,043,845 B2
(45) Date of Patent: Jul. 23, 2024

(54) METHODS OF CELL CULTURE

(71) Applicant: Polpharma Biologics S.A., Gdańsk (PL)

(72) Inventors: Louis Boon, Badhoevedorp (NL); Lenneke De Winter, Ede (NL); Tomasz Sitar, Gdańsk (PL)

(73) Assignee: Polpharma Biologics S.A., Gdańsk (PL)

(*) Notice: Subject to any disclaimer, the term of this patent is extended or adjusted under 35 U.S.C. 154(b) by 983 days.

(21) Appl. No.: 16/620,091

(22) PCT Filed: Jun. 8, 2018

(86) PCT No.: PCT/EP2018/065221
§ 371 (c)(1),
(2) Date: Dec. 6, 2019

(87) PCT Pub. No.: WO2018/224673
PCT Pub. Date: Dec. 13, 2018

(65) Prior Publication Data
US 2020/0199525 A1   Jun. 25, 2020

(30) Foreign Application Priority Data
Jun. 8, 2017 (EP) .................... 17460033

(51) Int. Cl.
*C12N 5/00* (2006.01)
*C12N 15/67* (2006.01)
(52) U.S. Cl.
CPC .......... *C12N 5/0018* (2013.01); *C12N 15/67* (2013.01); *C12N 2500/32* (2013.01); *C12N 2500/34* (2013.01)

(58) Field of Classification Search
CPC .. C12N 5/0018; C12N 15/67; C12N 2500/32; C12N 2500/34
See application file for complete search history.

(56) References Cited

U.S. PATENT DOCUMENTS

2008/0254513 A1* 10/2008 Cayli .................. C12N 5/0018
                                                            435/70.1
2017/0305999 A1* 10/2017 Leber .................. C12N 5/0018

FOREIGN PATENT DOCUMENTS

| CN | 106635953   | * | 5/2017 |
| CN | 106635953 A |   | 5/2017 |
| KR | 2003-0072764 A | | 9/2003 |

OTHER PUBLICATIONS

Bao et al., "An efficient protocol to enhance the extracellular production of recombinant protein from *Escherichia coli* by the synergistic effects of sucrose, glycine, and Triton X-100," *Protein Expression and Purification*, 126: 9-15 (May 14, 2016).

(Continued)

*Primary Examiner* — Blaine Lankford
*Assistant Examiner* — Lauren K Van Buren
(74) *Attorney, Agent, or Firm* — Leydig, Voit & Mayer, Ltd.

(57) ABSTRACT

The invention provide a method for reducing the amount of acidic species and/or increasing the amount of basic species in a composition comprising a recombinant protein or for increasing the specific production rate of mammalian cells expressing a recombinant protein to simplify subsequent clarification and purification of the recombinant protein, said method comprising culturing mammalian cells expressing said recombinant protein in a cell culture medium comprising citrulline.

8 Claims, 15 Drawing Sheets

(56) References Cited

OTHER PUBLICATIONS

Elhassan et al., "Amino acid concentrations in fluids from the bovine oviduct and uterus and in KSOM-based culture media," *Theriogenology*, 55(9): 1907-1918 (Jun. 1, 2001).

Spearman et al., "Components of yeast (*Sacchromyces cervisiae*) extract as defined media additives that support the growth and productivity of CHO cells," *J. of Biotechnology*, 233: 129-142 (May 7, 2016).

Wang et al., "Cultivation to improve in vivo solubility of overexpressed arginine deiminases in *Escherichia coli* and the enzyme characteristics," *BMC Biotechnology*, 14(1): 53 (Jun. 7, 2014).

European Patent Office, International Search Report in International Patent Application No. PCT/EP2018/065221, 6 pp. (Sep. 12, 2018).

European Patent Office, Written Opinion in International Patent Application No. PCT/EP2018/065221, 10 pp. (Sep. 12, 2018).

\* cited by examiner ively, the present invention relates to a method for reducing the
METHODS OF CELL CULTURE

CROSS-REFERENCE TO RELATED APPLICATIONS

This application is the U.S. national phase of International Patent Application PCT/EP2018/065221, filed 08 Jun. 2018, which claims the benefit of European Patent Application 17460033.8, filed Jun. 8, 2017, both of which are hereby incorporated by reference in their entireties herein.

FIELD OF THE INVENTION

The present invention relates to a method for reducing the amount of acidic species and/or increasing the amount of basic species in a composition comprising a recombinant protein or for increasing the size of mammalian cells expressing a recombinant protein or for increasing the specific production rate of mammalian cells expressing a recombinant protein to simplify subsequent clarification and purification of the recombinant protein, said method comprising culturing mammalian cells expressing said recombinant protein in a cell culture medium comprising citrulline.

BACKGROUND OF THE INVENTION

In the last 20 years, the use of therapeutic antibodies for the treatment of different diseases such as inflammatory diseases and cancer has become increasingly more important and the first biosimilar antibody products are already marketed.

The production of therapeutic proteins and in particular of therapeutic antibodies involves the use of cell cultures which may result in the production of proteins which are heterogenous in their biochemical and biophysical characteristics due to post-translational and degradation events. Such heterogeneity includes the presence of acidic and/or basic species which may be detected by isoelectric focussing or ion exchange chromatography and which may affect product stability. Further, in biosimilar products the amount of acidic and basic species should be controlled and if possible correspond to the amount of acidic and basic species in the originator product as much as possible. Hence, there is a need for methods for modulating the amount of acidic and basic species. Additionally, there is also a need for methods which increase the specific protein production rate in the mammalian host cells.

The prior art discloses various methods for reducing the amount of acidic species in a composition of a recombinant protein.

US 2016/0039925 A1 discloses a method for controlling the amount of acidic species by adding one or more amino acids selected from arginine, lysine, ornithine and histidine to the cell culture medium.

CN 104560882 A describes a method for reducing the acidic peak level by using different basal media and concentrated culture media in the cell culture process.

CN 105779394 A discloses a method for reducing the acidic peak content by using GS-CHO cells as expression system and adding glutamine to the basic medium.

Nevertheless, there is still a need for a cell culture process which enables a more precise control of the amount of acidic and basic species, in particular in the development of biosimilar products where the level of acidic and basic species in the biosimilar product should be comparable to that of the reference product.

SUMMARY OF THE INVENTION

The present inventors have found that by adding citrulline to the cell culture medium the amount of acidic species can be reduced and/or the amount of basic species can be increased.

Additionally, they found that the addition of citrulline to the cell culture medium increases the size and in particular the volume of the mammalian cells being cultured and the specific production rate of the mammalian cells for the recombinant protein.

The inventors have also observed that the cell culture fluid obtained from cells cultured in the presence of citrulline shows a better filterability in depth filtration compared to the cell culture fluid obtained from cells cultured in the absence of citrulline, i.e. that a higher volume of the cell culture supernatant can be filtered through the same filter size.

Another observation of the inventors is that the filtrate obtained by depth filtration of a cell culture fluid obtained from cells cultured in the presence of citrulline has less host cell-derived components such as host cell-derived proteins than a filtrate obtained by depth filtration of a cell culture fluid obtained from cells cultured in the absence of citrulline.

CN 106635953 A discloses a serum-free culture medium comprising amino acids, vitamins, inorganic salts, trace elements, carbohydrates, polyamines which may include citrulline and hydrolysates.

Spearman et al. (2016) J. Biotechnol. 233: 129-142 describes the fractionation of yeast lysate and the characterization of its components. Citrulline did not show a positive effect in one cell line, while it enhanced growth in another cell line.

Wang et al. (2014) describes the expression of arginine deiminase which catalyzes the conversion of arginine to citrulline in E. coli.

In Elhassan et al. (2001) Theriogenology 55(9): 1907-1918 the amino acid concentrations in bovine oviductal and uterine fluids were measured and compared to the concentrations in modified simplex optimized medium supplemented with different additives.

In Bao et al. (2016) Protein Expr. Purif. 126: 9-15 the effect of adding sucrose, glycine and Triton X-100 to the culture medium of E. coli cells is investigated.

KR 2003 0072764 A relates to a method of culturing transformed plant cells which produce a recombinant protein.

Accordingly, the present invention relates to a method for reducing the amount of acidic species in a composition comprising a recombinant protein, said method comprising culturing mammalian cells expressing said recombinant protein in a cell culture medium comprising citrulline.

The present invention also relates to a method for increasing the amount of basic species in a composition comprising a recombinant protein, said method comprising culturing mammalian cells expressing said recombinant protein in a cell culture medium comprising citrulline.

Further, the present invention relates to a method for reducing the amount of acidic species and increasing the percentage of basic species in a composition comprising a recombinant protein, said method comprising culturing mammalian cells expressing said recombinant protein in a cell culture medium comprising citrulline.

The present invention also relates to a method for increasing the amount of basic species and/or for reducing the amount of acidic species in a composition comprising natalizumab or ustekinumab, said method comprising culturing mammalian cells expressing natalizumab or ustekinumab in a cell culture medium comprising citrulline.

The present invention also relates to a method for increasing the size of eukaryotic cells, said method comprising culturing said cells expressing said recombinant protein in a cell culture medium comprising citrulline and/or sucrose.

In one embodiment the increase in cell size is measured as an increase in cell volume.

Further, the present invention relates to a method for increasing the specific production rate of eukaryotic cells expressing a recombinant protein, said method comprising culturing said cells expressing said recombinant protein in a cell culture medium comprising citrulline and/or sucrose.

The present invention also relates to a method for decreasing apoptosis of mammalian cells, said method comprising culturing said cells in a cell culture medium comprising citrulline and/or sucrose.

In one embodiment the cell culture medium comprises 2 to 30 g/l citrulline.

In one embodiment the cell culture medium comprises 5 to 80 mM sucrose. The sucrose may be added to the cell culture medium.

In one embodiment the cell culture medium comprises 2 to 30 g/l citrulline and 5 to 80 mM sucrose.

The cells may be cultured in fed-batch mode using first a basal medium and then a feed medium. Both the basal medium and the feed medium may comprise citrulline.

The citrulline may be added to the cell culture medium.

In one embodiment no additional lysine is added to the cell culture medium.

In one embodiment the temperature is changed from a first temperature to a second temperature during the culturing. The second temperature may be from 25° C. to 36° C.

The recombinant protein may be a recombinant antibody. The eukaryotic cells may be mammalian cells and in particular the eukaryotic cells may be Chinese Hamster Ovary cells.

The present invention also relates to a method of producing a composition comprising a recombinant antibody in Chinese Hamster Ovary cells expressing said antibody, the method comprising:
(a) culturing said cells in a cell culture medium comprising 2 to 30 g/l citrulline; and
(b) obtaining the composition comprising the antibody from the cell culture medium.

In one embodiment the composition has a reduced amount of acidic species of the antibody compared to a composition produced by culturing said cells in a cell culture medium not comprising 2 to 30 g/l citrulline.

The cell culture medium may further comprise 5 to 80 mM sucrose.

In one embodiment no additional lysine is added to the cell culture medium.

The cells may be cultured in fed-batch mode using first a basal medium and then a feed medium and both the basal medium and the feed medium may comprise citrulline.

The citrulline may be added to the cell culture medium.

In one embodiment the temperature is changed from a first temperature to a second temperature during the culturing. The second temperature may be from 25° C. to 36° C.

The present invention also relates to the use of a cell culture medium comprising citrulline for reducing the amount of acidic species and/or increasing the amount of basic species in a composition comprising a recombinant protein.

The present invention also relates to the use of a cell culture medium comprising citrulline for increasing the size of mammalian cells expressing a recombinant protein.

The present invention also relates to the use of a cell culture medium comprising citrulline for increasing the specific production rate of mammalian cells expressing a recombinant protein.

In one embodiment of said uses the cell culture medium comprises 2 to 30 g/l citrulline. In one embodiment of said uses the cell culture medium comprises 5 to 80 mM sucrose.

The cells were cultured without citrulline (control), 5 g/l and 8 g/l for 12 or 14 days and the glycan composition was analyzed afterwards. For each of the conditions, the bars show from left to right: G0F (%), G1F (%), G1'F (%), G2F (%) and sum sialylated.

Figure 5A:
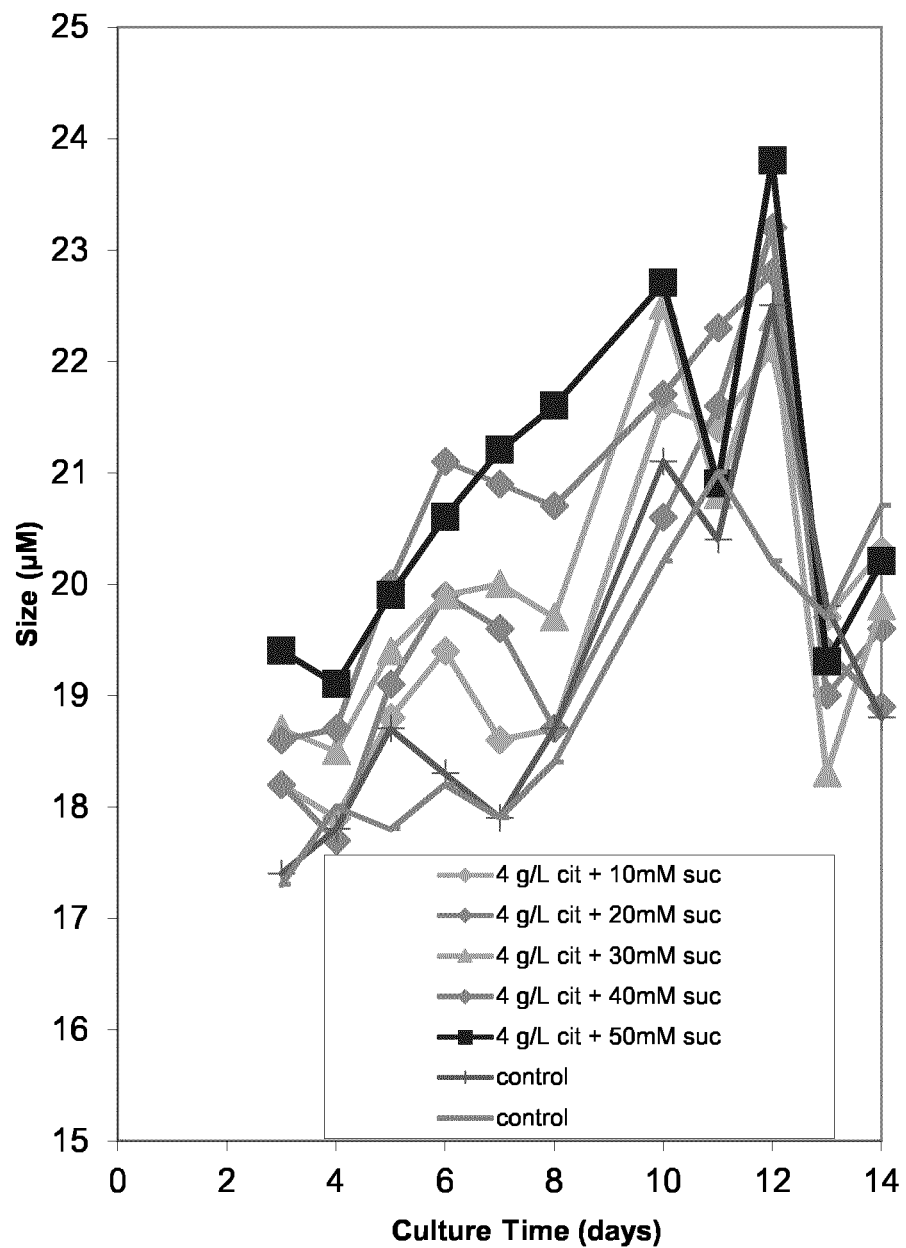
Figure 5B:
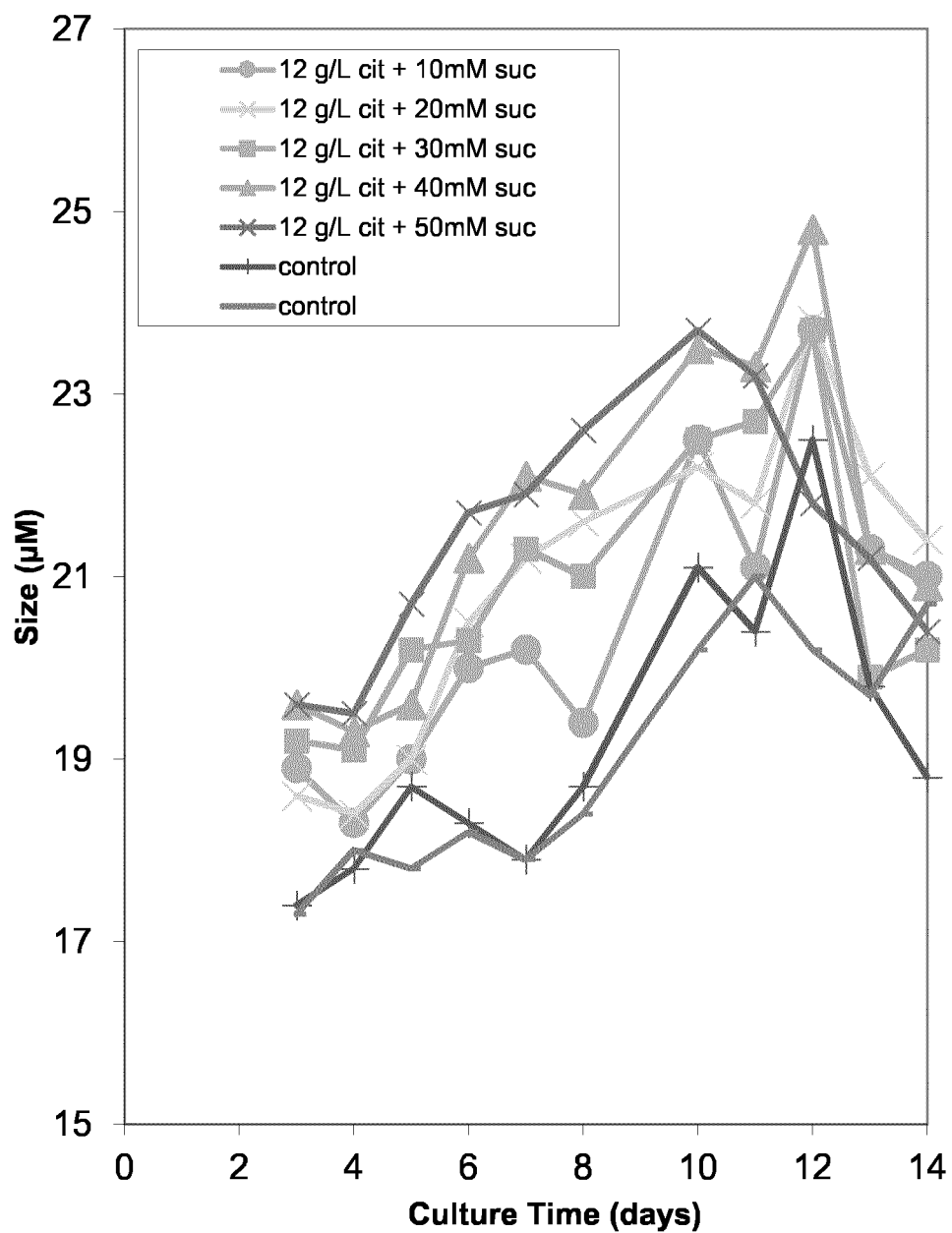

FIG. 5A: Cell diameter of CHO cells producing ustekinumab cultured in a cell culture medium containing 4 g/l of citrulline and different concentrations of sucrose or not containing citrulline and sucrose (control) dependent on the culture time. FIG. 5B: Cell diameter of CHO cells producing ustekinumab cultured in a cell culture medium containing 12 g/l of citrulline and different concentrations of sucrose or not containing citrulline and sucrose (control) dependent on the culture time.

Figure 6A:
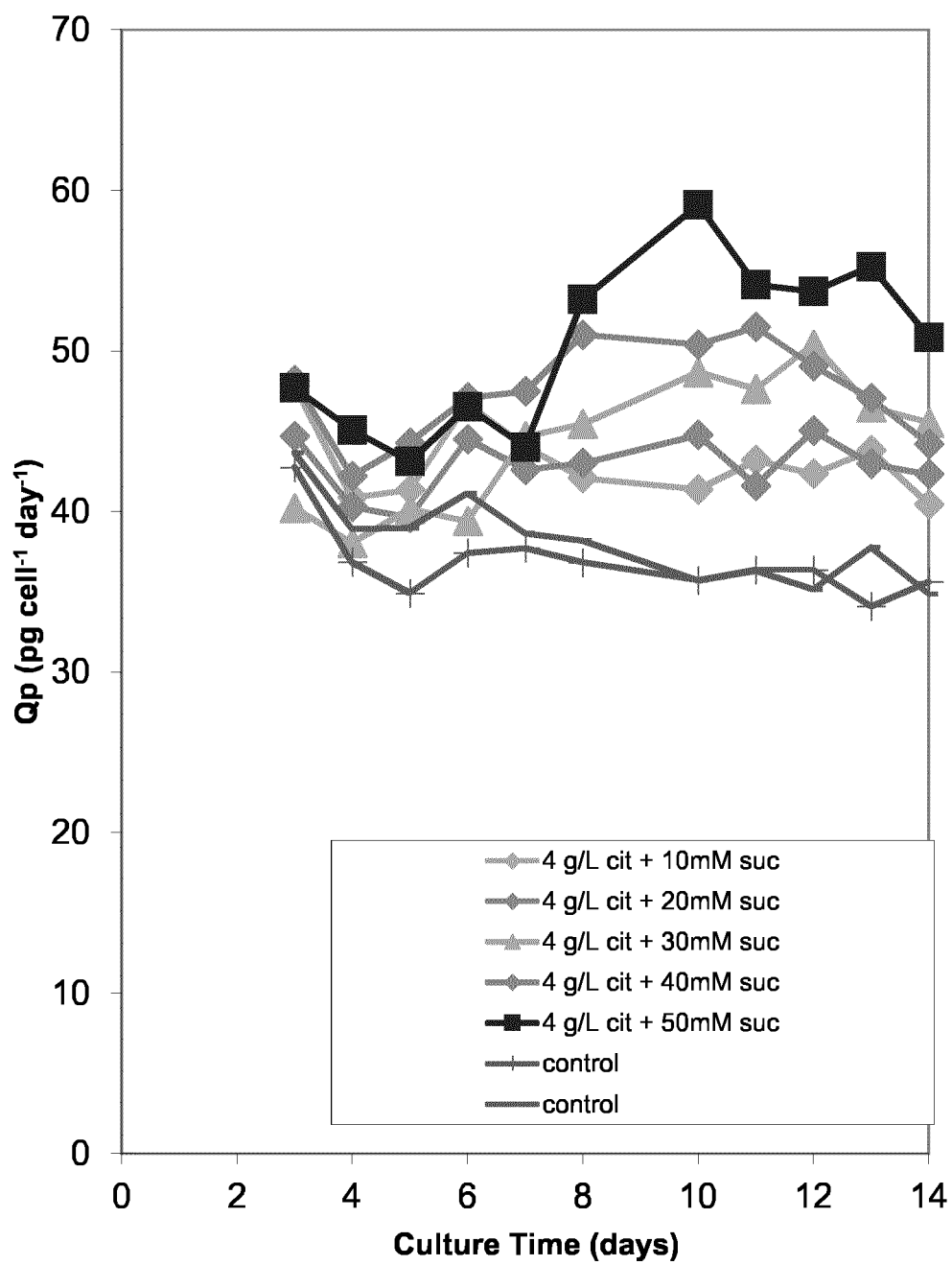
Figure 6B:
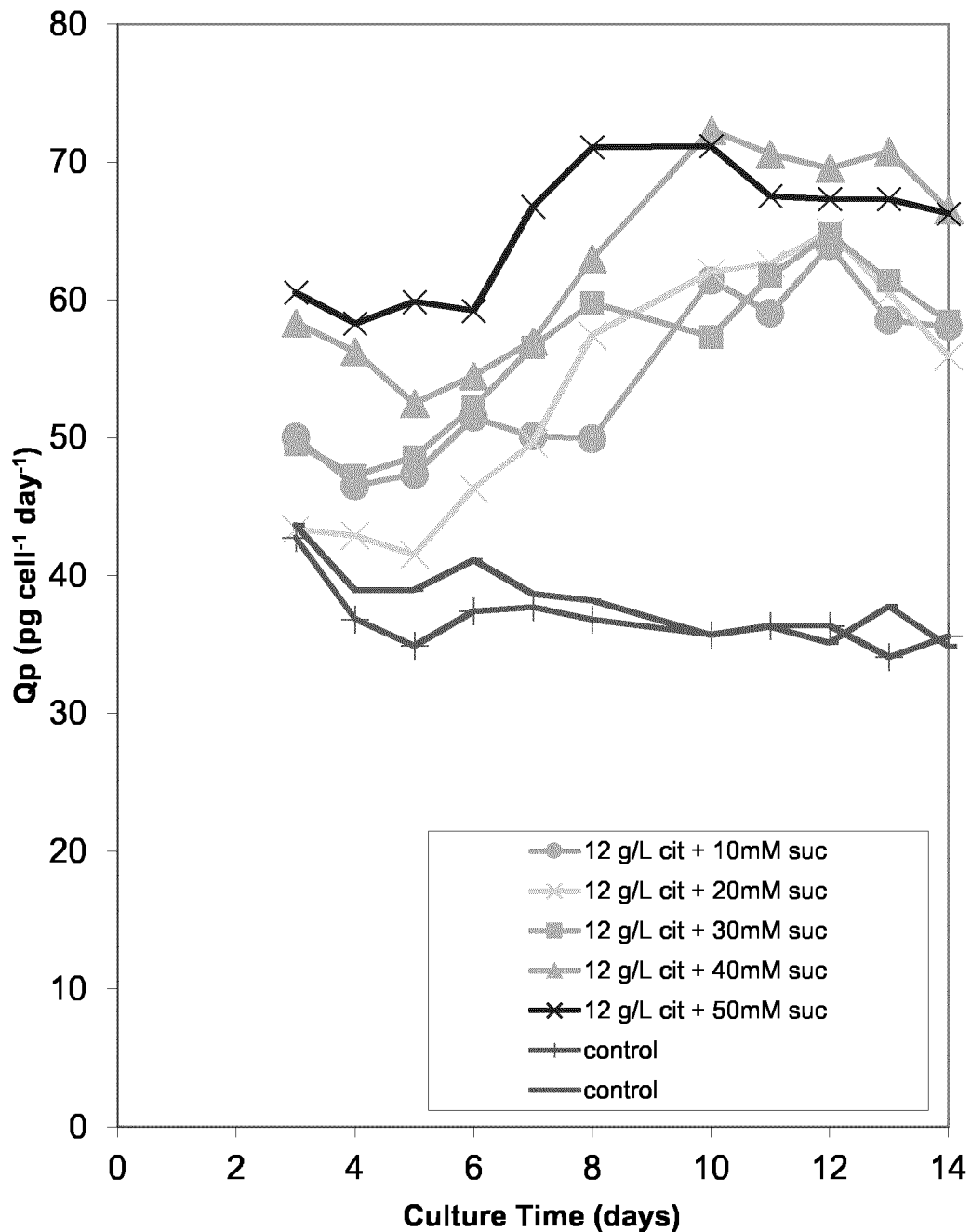

FIG. 6A: Specific production rate (Qp) of CHO cells producing ustekinumab cultured in a cell culture medium containing 4 g/l of citrulline and different concentrations of sucrose or not containing citrulline and sucrose (control) dependent on the culture time. FIG. 6B: Specific production rate (Qp) of CHO cells producing ustekinumab cultured in a cell culture medium containing 12 g/l of citrulline and different concentrations of sucrose or not containing citrulline and sucrose (control) dependent on the culture time.

Figure 7:
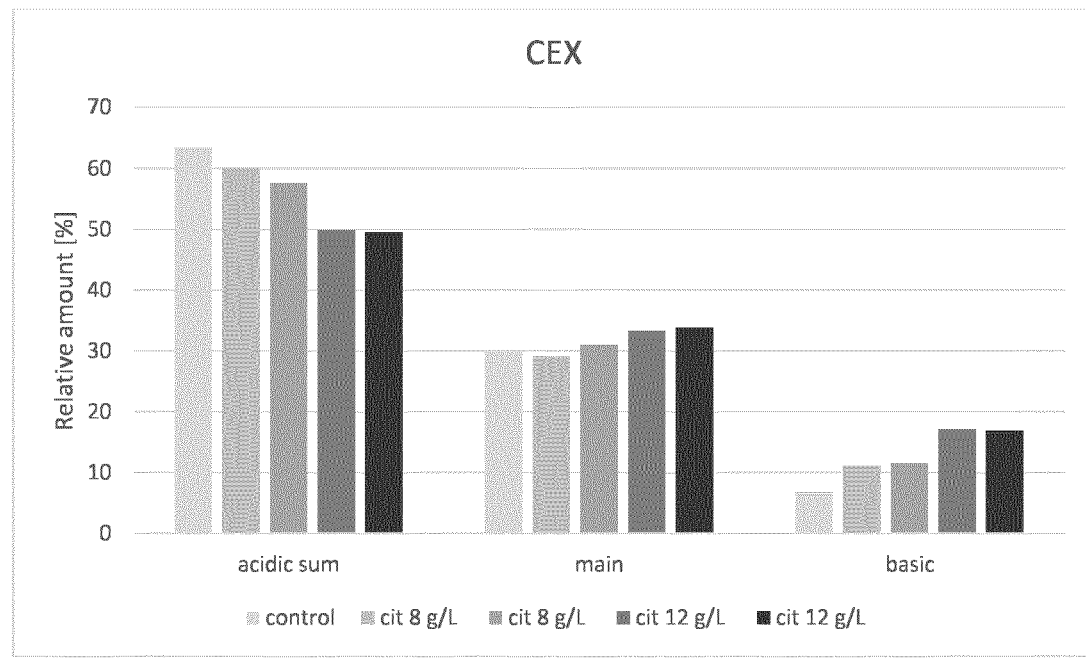

FIG. 7: Analysis of acidic species, main species and basic species in the natalizumab antibody produced in CHO cells by cation exchange chromatography.

The cells were cultured without citrulline (control), 8 g/l and 12 g/l citrulline for 14 days. For each of the species, the bar graphs show from left to right: control, experiment 1 with 8 g/l citrulline, experiment 2 with 8 g/l citrulline, experiment 1 with 12 g/l citrulline and experiment 2 with 12 g/l citrulline.

Figure 8:
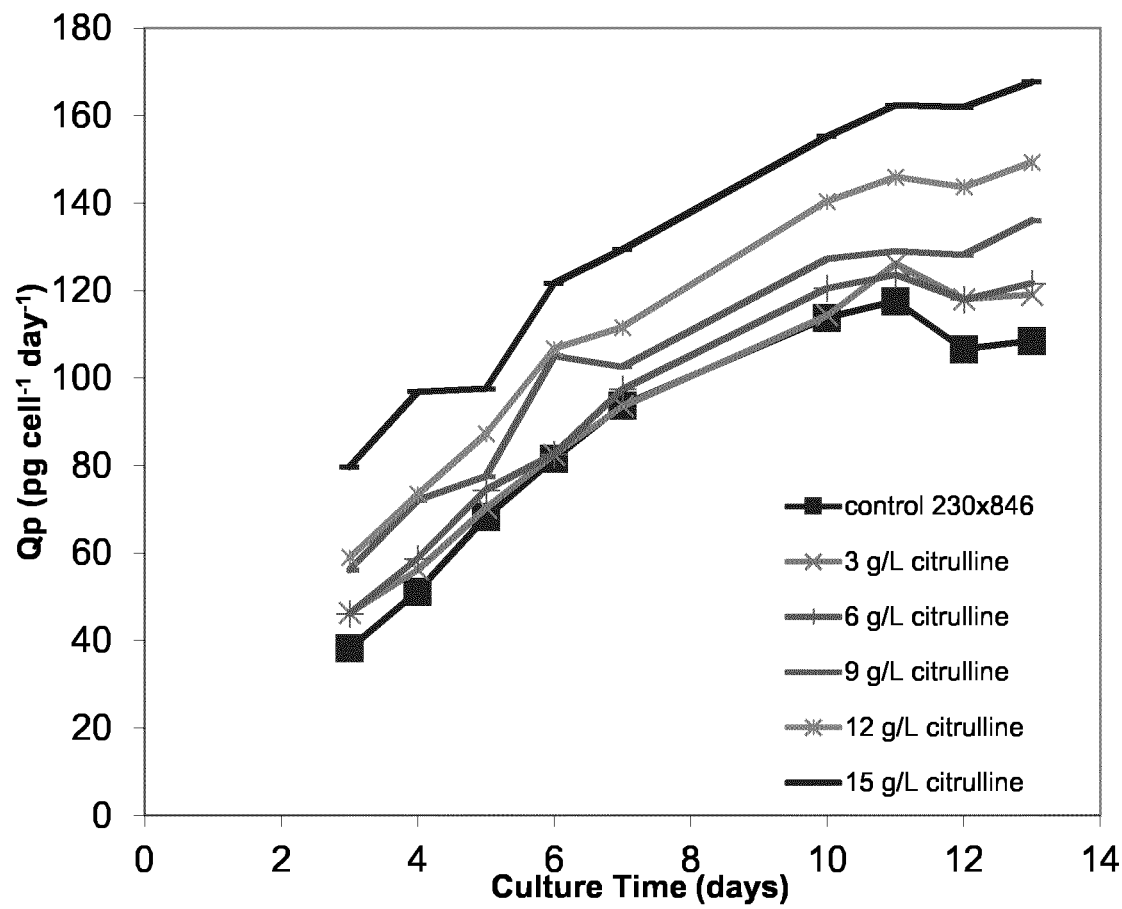

FIG. 8: Specific production rate (Qp) of CHO cells producing omalizumab cultured in a cell culture medium containing different concentrations of citrulline or not containing citrulline (control) dependent on the culture time.

Figure 9:
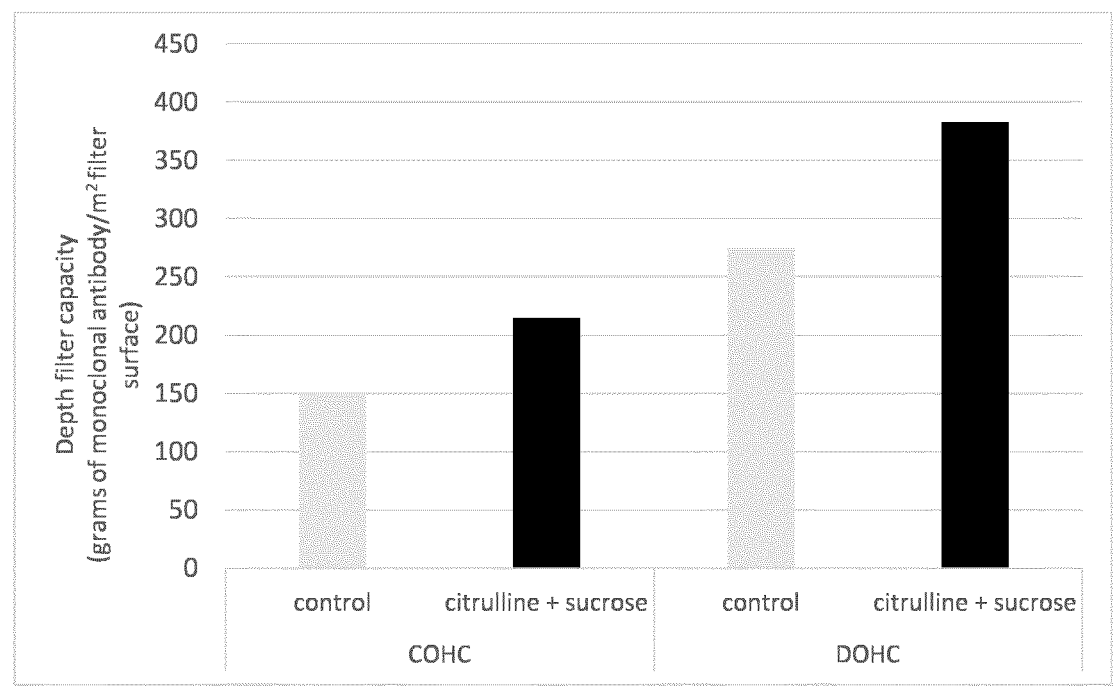

FIG. 9: Depth filter capacities determined at the point of 1 bar pressure build-up are shown in FIG. 9. The capacity units are grams of monoclonal antibody (omalizumab) per square meter of filter surface.

Figure 10:
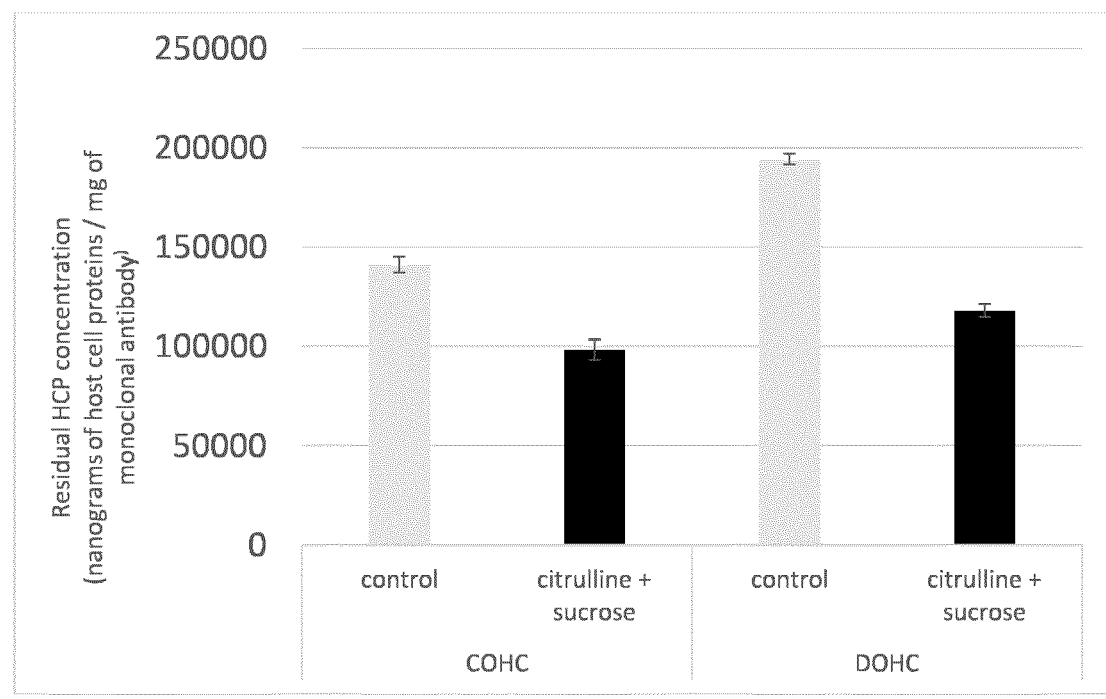

FIG. 10: Residual host cell protein (HCP) concentrations measured by ELISA are depicted in FIG. 10. Filtrates of both control harvest and cultured in the presence of citrulline and sucrose are shown in parts per million (nanograms of host cell protein per milligram of monoclonal antibody (omalizumab).

Figure 11:
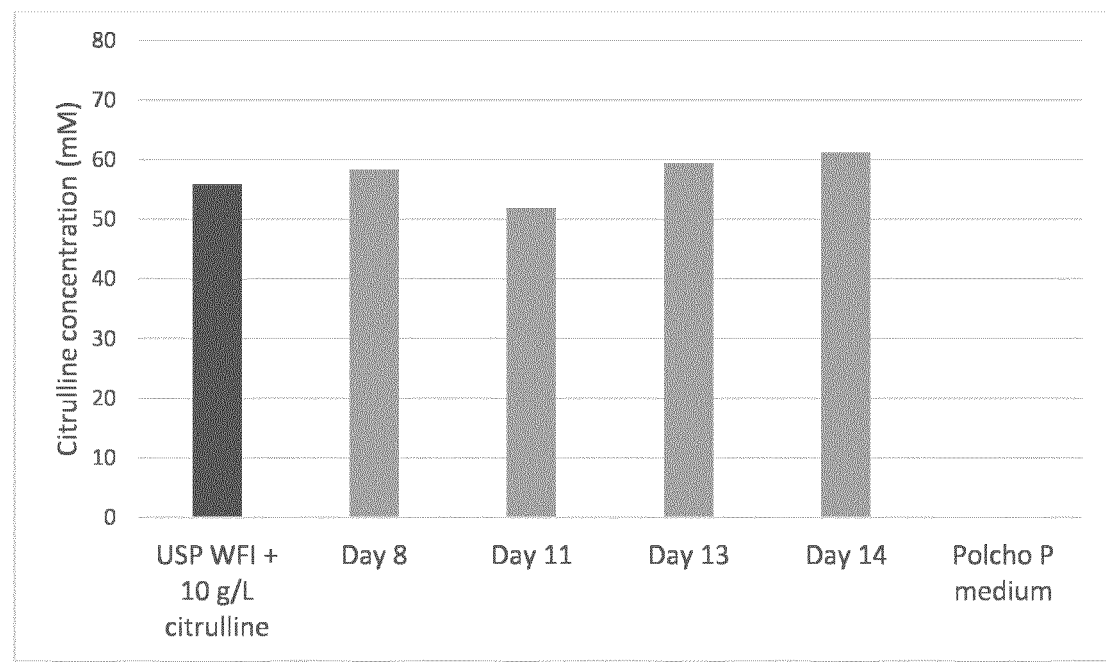

FIG. 11: Citrulline concentrations in basal medium and at different timepoints during the fermentation of cell line C69 in stirred tank reactors, relative to the same concentration of citrulline (10 g/l) in WFI.

Figure 12A:
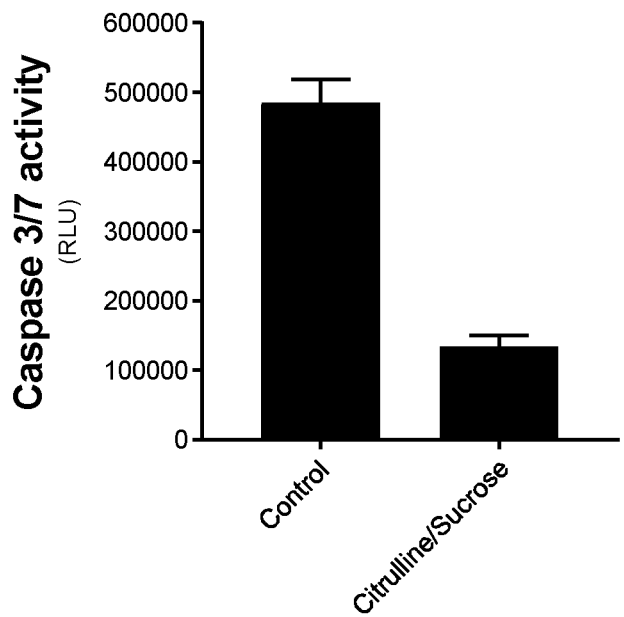
Figure 12B:
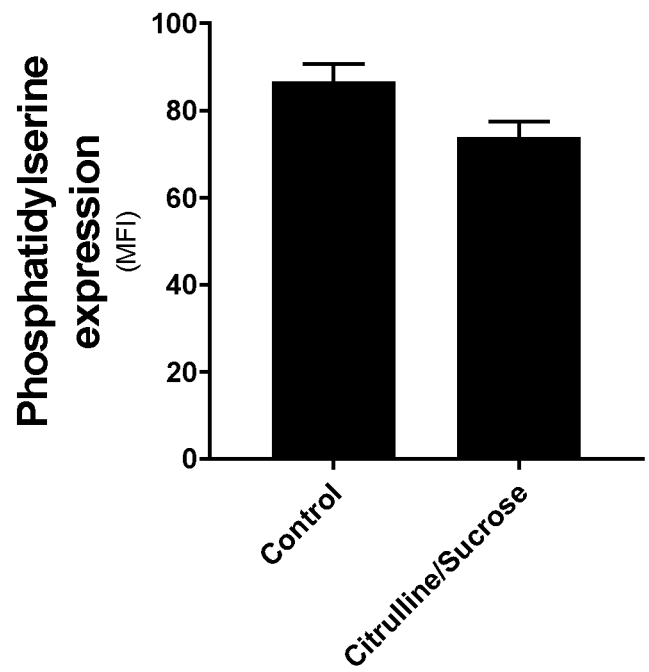
Figure 12:
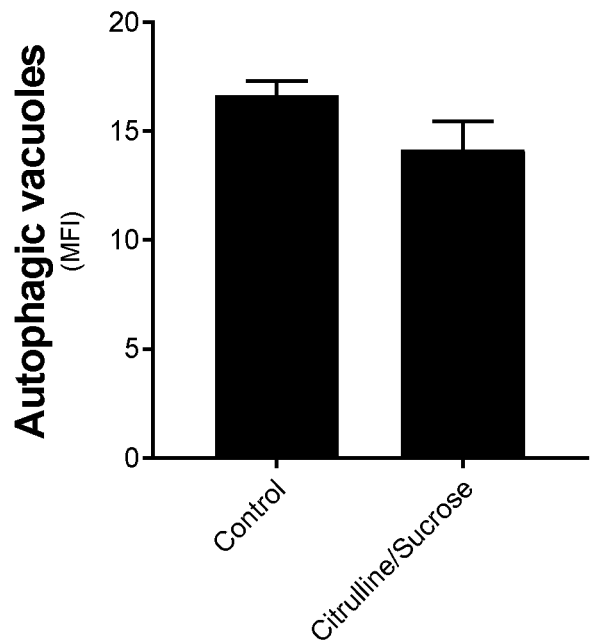
Figure 12D:
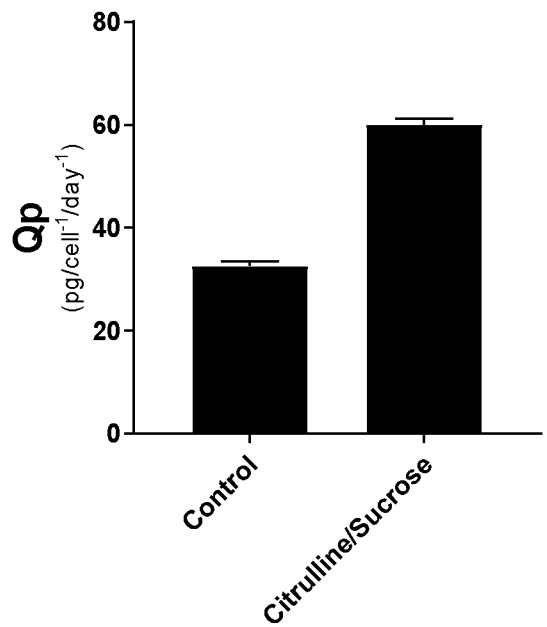

FIG. 12A: Effect of citrulline/sucrose treatment for 11 days on early apoptosis (caspase 3/7 activity of CHO cells producing ustekinumab. Mean+SD (n=4) is shown. FIG. 12B: Effect of citrulline/sucrose treatment for 11 days on early apoptosis (outer membrane phosphatidylserine expression levels) of CHO cells producing ustekinumab. Mean+SD (n=4) is shown. FIG. 12C: Effect of citrulline/sucrose treatment for 11 days on autophagy (intracellular autophagic vacuole expression levels) of CHO cells producing ustekinumab. Mean+SD (n=4) is shown. FIG. 12D: Effect of citrulline/sucrose treatment for 11 days on the specific production rate of (D, Qp) CHO cells producing ustekinumab. Mean+SD (n=4) is shown.

DETAILED DESCRIPTION OF THE INVENTION

Although the present invention will be described with respect to particular embodiments, this description is not to be construed in a limiting sense.

Before describing in detail exemplary embodiments of the present invention, definitions important for understanding the present invention are given. Unless stated otherwise or apparent from the nature of the definition, the definitions apply to all methods and uses described herein.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As discussed above, the present invention is based on the finding that the addition of citrulline to the cell culture medium reduces the amount of acidic species in a composition comprising a recombinant protein. Additionally or alternatively, the addition of citrulline may increase the amount of basic species in a composition comprising a recombinant protein. The reduction of the amount of acidic species in a composition comprising a recombinant protein and/or the increase of the amount of basic species in a composition comprising a recombinant protein is compared to a composition comprising said recombinant protein produced in mammalian cells cultured in a cell culture medium not comprising citrulline.

The term "reduction of the amount of acidic species" is intended to mean that the amount of acidic species in a composition comprising a recombinant protein is lower when the composition is produced in a cell culture medium comprising citrulline compared to the amount of acidic species in a composition comprising the same recombinant protein which is produced in a cell culture medium not comprising citrulline.

The term "acidic species" refers to variants of the recombinant protein which elute earlier than the main peak from a cation exchange column and later than the main peak from an anion exchange column. The acidic species may elute as a single peak or in more than one peak, such as in two distinctive peaks. The acidic species may be formed by the addition of sialic acids, the deamidation of asparagine residues, the formation of non-classical disulfide linkages or trisulfide bonds, high mannose content, thiosulfide modification, glycation, modification by maleuric acid, cysteinylation, the formation of reduced disulfide bonds, non-reduced species and fragments. The most common reasons for the formation of acidic species are the addition of sialic acids and deamidation of asparagine residues.

The "main species" is the species of the recombinant protein which elutes as the major peak on chromatograms. The main species does not necessarily correspond to the unmodified or non-degraded recombinant protein, but may also comprise post-translational modifications. If the recombinant protein is a recombinant antibody, the main species typically includes antibodies comprising a cyclization of the N-terminal glutamine, the removal of the heavy chain C-terminal lysine and a glycosylation of the conserved asparagine residue in the CH2 domain with neutral oligosaccharides.

The term "basic species" refers to variants of the recombinant protein which elute later than the main peak from a cation exchange column and earlier than the main peak from an anion exchange column. The main reasons for the formation of basic species are incomplete removal of the C-terminal lysine of the heavy chain, incomplete cyclization of the N-terminal glutamine of the light or heavy chain or of both, isomerization of aspartate and the presence of succinimide. Additional modifications resulting in the formation of basic species are oxidation of the two conserved methionine residues in the Fc region, amidation of the proline residue after removal of the heavy chain C-terminal lysine, incomplete formation of disulfide bonds, incomplete removal of leader sequence, mutation from serine to arginine, aglycosylation and the formation of fragments and aggregates.

The acidic species, main species and basic species are preferably detected by cation exchange chromatography. The cation exchange chromatography resin can be grafted with sulfonate for strong cation exchange and with carboxylic acid groups for weak cation exchange. Suitable strong cation exchange resins include Proteomix SCX-NP1.7 available from Sepax and Waters Protein-Pak Hi Res SP available from Waters. Suitable weak cation exchange resins include ProPac WCX-10 available from Thermo Scientific.

The composition comprising the recombinant protein is loaded on the cation exchange chromatography column in a suitable loading buffer and eluted from the column using a pH gradient, a salt gradient or a combination of a pH and salt gradient. Suitable conditions are described in the examples section below. The acidic species, main species and basic species are detected at 220 nm or 280 nm.

The relative amount as percentage of total proteinaceous species present of acidic species, main species and basic species as defined above can be calculated from the area under the corresponding peak in the elution profile of the cation exchange chromatography.

Before the composition comprising the recombinant protein is analyzed for the presence of acidic and basic species, the recombinant protein may be purified. If the recombinant protein is a recombinant antibody or a Fc-containing protein, it may be purified using protein A.

The method of the present invention leads to a reduction of the amount of acidic species after 14 days of culture by at least 2% or 5%, preferably by at least 7% or 9%, more preferably by at least 12% or 15% and most preferably by at least 20%, 22% or 24% compared to the amount of acidic species in a composition produced by culturing the cells in a cell culture medium not comprising citrulline. The above percentages are calculated by the following formula:

100−amount of acidic species in presence of citrulline/amount of acidic species in absence of citrulline*100.

Alternatively or additionally, the method of the present invention leads to an increase of the amount of basic species after 14 days of culture by at least 10% or 20%, preferably by at least 30% or 40%, more preferably by at least 50% or 60% and most preferably by at least 70%, 80% or 90% compared to the amount of basic species in a composition produced by culturing the cells in a cell culture medium not comprising citrulline. The above percentages are calculated by the following formula: amount of basic species in presence of citrulline/amount of basic species in absence of citrulline*100-100.

The term "recombinant protein" refers to any protein which can be produced by mammalian cell culture as the result of the transcription and translation of a gene encoding said recombinant protein which gene is carried on a recombinant nucleic acid molecule that has been introduced into the mammalian host cell. The recombinant protein may not be produced naturally in the mammalian cells used or the recombinant protein may be produced naturally in the mammalian cells used, but at a lower level so that the recombinant cell can be distinguished from the non-modified, non-recombinant cell by the higher expression level of the recombinant protein compared to the expression level in a non-modified, non-recombinant cell. Preferably, the recombinant protein is not produced naturally by the mammalian cell.

In particular, the term "recombinant protein" encompasses therapeutic proteins such as cytokines, growth factors, clotting factors, vaccines and antibodies. Preferably, the recombinant protein is an Fc containing protein such as an antibody or a fusion protein of the Fc portion of an IgG antibody with parts or all of another protein.

Examples of a fusion protein of the Fc portion of an IgG antibody with parts or all of another protein include, but are not limited to, etanercept and lenercept (fusion with TNF receptor), aflibercept and conbercept (fusion with extracellular domains of VEGF receptors 1 and 2), abatacept and belatacept (fusion with extracellular domain of CTLA-4) and rilonacept (fusion with extracellular portions of the human interleukin-1 receptor component (IL-1R1) and IL-1 receptor accessory protein (IL-1RAcP)).

More preferably, the recombinant protein is a recombinant antibody. The term "recombinant antibody" refers to any antibody which can be produced by mammalian cell culture as the result of the transcription and translation of a gene encoding said recombinant antibody which gene is carried on a recombinant nucleic acid molecule that has been introduced into the mammalian host cell. The recombinant antibody may not be produced naturally in the mammalian cells used or the recombinant antibody may be produced naturally in the mammalian cells used, but at a lower level so that the recombinant cell can be distinguished from the non-modified, non-recombinant cell by the higher expression level of the recombinant antibody compared to the expression level in a non-modified, non-recombinant cell. Preferably, the recombinant antibody is not produced naturally by the mammalian host cell used for its production.

The terms "immunoglobulin" and "antibody" are used interchangeably herein. The immunoglobulin may be a monoclonal antibody, multispecific antibody (e.g. bispecific antibody) or fragments thereof exhibiting the desired antigen binding activity. Naturally occurring antibodies are molecules with varying structures. For example, native IgG antibodies are heterotetrameric glycoproteins of about 150,000 Daltons, composed of two identical light chains and two identical heavy chains that are linked by disulfide bonds. From N- to C-terminus, each heavy chain has a variable domain (VH), also called a variable heavy domain or a heavy chain variable domain followed by three or four constant domains (CH1, CH2, CH3 and optionally CH4). Similarly, from N- to C-terminus, each light chain has a variable domain (VL), also called a variable light domain or a light chain variable domain followed by a constant light chain (CL) domain. The light chain of an antibody may be assigned to one of two types, called kappa (κ) and lambda (λ), based on the amino acid sequence of its constant domain.

"Antibody fragments" comprise a portion of a full-length antibody, generally the antigen binding or variable region thereof. Examples of antibody fragments include Fab, Fab', F(ab')2, and Fv fragments, single-chain antibody molecules, diabodies, linear antibodies and multispecific antibodies formed from antibody fragments.

Preferably, the immunoglobulin is a monoclonal antibody. The term "monoclonal antibody" as used herein refers to an antibody obtained from a population of substantially homogeneous antibodies, i.e. the individual antibodies of the population are identical except for possible naturally occurring mutations that may be present in minor amounts. In contrast to polyclonal antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The immunoglobulin may be of the murine classes IgG1, IgG2a, IgG2b, IgM, IgA, IgD or IgE, the human classes IgG1, IgG2, IgG3, IgG4, IgM, IgA1, IgA2, IgD or IgE, or combinations or fragments thereof.

The immunoglobulin may recognize any one or a combination of proteins including, but not limited to the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, CD152, IL-1a, IL-1β, IL-1, IL-2, IL-3, IL-7, IL-4, IL-5, IL-8, IL-10, IL-12, IL-23, IL-2 receptor, IL-4 receptor, IL-6 receptor, IL-12 receptor, IL-13 receptor, IL-18 receptor subunits, PDGF-β, and analogues thereof, PLGF, VEGF, TGF, TGF-β2, TGF-p1, EGF receptor, PLGF receptor, VEGF receptor, platelet receptor gpIIb/IIIa, thrombopoeitin receptor, apoptosis receptor PD-1, hepatocyte growth factor, osteoprotegerin ligand, interferon gamma, B lymphocyte stimulator BLyS, T-cell activation regulator CTLA-4, C5 complement, IgE, tumor antigen CA125, tumor antigen MUC1, PEM antigen, ErbB2/HER-2, tumor-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, α4β1 and α4β7 integrin, TRAIL receptors 1,2,3, and 4, RANK, a RANK ligand (RANKL), TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, sclerostin, MHC I, carcinoembryonic antigen (CEA), alpha-fetoprotein (AFP), tumor necrosis factor (TNF), Fc-γ-1 receptor, HLA-DR 10 beta, HLA-DR antigen, L-selectin, and IFN-γ.

The immunoglobulin may for example be afelimomab, abciximab, adalimumab, alemtuzumab, arcitumomab, belimumab, canakinumab, cetuximab, denosumab, trastuzumab, imciromab, capromab, infliximab, ipilimumab, abciximab, rituximab, basiliximab, palivizumab, natalizumab, nivolumab, nofetumomab, omalizumab, daclizumab, ibritumomab, muromonab-CD3, edrecolomab, gemtuzumab, golimumab, certolizumab, eculizumab, ustekinumab, ocrelizumab, ofatumumab, obinutuzumab, panitumumab, pertuzumab, ranibizumab, romosozumab, tocilizumab, tositumomab, clenoliximab, keliximab, galiximab, foravirumab, lexatumumab, bevacizumab, satumomab, catumaxomab, brentuximab, raxibazumab, tosimumab, efalizumab, motavizumab, bezlotoxumab, ixekizumab, olaratumab, pembrolizumab, secukinumab and vedolizumab.

The immunoglobulin of the invention is preferably an IgG molecule, such as an IgG1, IgG2, IgG3, or IgG4 molecule. More preferably, the immunoglobulin is IgG1 or IgG4. Even more preferably, the immunoglobulin is an IgG1 wherein at least the Fc part is human.

The immunoglobulin may be a murine-human chimeric IgG1 wherein the Fc part of the IgG1 is human and the variable region is of mouse origin.

Alternatively, the immunoglobulin may be a humanized IgG1 or IgG4 form of a murine progenitor in that the CDRs of the variable domain are derived from mouse and the framework regions of the variable domain are derived from human. Most preferably, the humanized antibody is natalizumab or omalizumab. Natalizumab is a humanized antibody binding to α4 integrin which is described in detail in, for example, WO 95/19790 A1. Omalizumab is a humanized antibody binding to IgE which is described in detail in, for example, WO 93/04173 A1.

Alternatively, the immunoglobulin may be a fully human IgG1 antibody, i.e. an antibody in which all parts are derived from human origin. Most preferably the human antibody is ustekinumab. Ustekinumab is a human anti-IL12 and anti-IL23 antibody binding to the p40 subunit of both human IL12 and human IL23 which is described in detail in, for example, WO 02/12500 A2.

In one embodiment the antibody may be natalizumab, omalizumab or ustekinumab.

In the method of the present invention the recombinant protein is produced in eukaryotic cells and in particular in mammalian cells. Suitable mammalian cells for expressing the recombinant protein in the method of the present invention include Chinese Hamster Ovary (CHO) cells, NSO myeloma cells, COS cells, SP2 cells, monkey kidney CV1, human embryonic kidney cell (293), baby hamster kidney cells (BHK), mouse Sertoli cells (TM4), African green monkey kidney cells (VERO-76), human cervical carcinoma cells (HeLa), canine kidney cells (MDC), buffalo rat liver cells (BRL 3 A), human lung cells (W138), human liver cells (Hep G2), mouse mammary tumor cells (MMT 060562), TRI cells, MRC 5 cells and FS4 cells.

Preferably, the mammalian cells are derived from a rodent selected from hamster and mouse.

More preferably, the mammalian cells are Chinese hamster ovary (CHO) cells such as CHO-K1, CHO-DUKX (dihydrofolate reductase (DHFR)-deficient CHO cells), CHO-pro3 (proline-dependent cells) and CHO-DG44 (dihydrofolate reductase (DHFR)-deficient and proline-dependent cells).

Even more preferably the cells are CHO-K1 cells. The CHO-K1 cell line has been obtained from a single clone of the original CHO cells (Kao and Puck (1968) Proc. Nat. Acad. Sci. USA 60(4): 1275-1281). The CHO-K1 cell line can be adapted to suspension growth and/or to a chemically defined medium (see, e.g., Bort et al. (2010) Biotechnol. J. 5(10): 1090-1097). In the present invention preferably CHO-K1 cells or cells derived therefrom are used. The cells which are derived from the CHO-K1 cells are cells which originate from the CHO-K1 cells, but have been subjected to one or more adaptation processes, such as adaptation to serum-free medium or suspension growth.

The mammalian cells have been transformed, i.e. genetically modified, with at least one recombinant nucleic acid molecule such as an expression vector which enables the stable production of the recombinant protein in the mammalian host cells. Due to the presence of the recombinant nucleic acid molecule the transformed or recombinant cells can be distinguished from untransformed or non-recombinant cells.

In the production of recombinant antibodies the mammalian cells may either be transformed with one recombinant nucleic acid molecule which encodes both the heavy and the light chain of the antibody or with two recombinant nucleic acid molecules of which one encodes the light chain of the antibody and the other one encodes the heavy chain of the antibody.

The elements and methods needed to construct expression vectors which are suitable for expressing a recombinant protein such as a recombinant antibody in mammalian cells, preferably in CHO cells, are well-known to the skilled person and described for example in Makrides et al. (1999) Protein Expr. Purif. 17: 183-202 and Kaufman (2000) Mol. Biotechnol. 16: 151-161. Further, the skilled person is aware of methods for introducing the expression vectors into the mammalian cells. These methods include the use of commercially available transfection kits such as Lipofectamine® of ThermoFisher, PEImax of Polyplus Sciences) or Freestyle Max of Invitrogen. Further suitable methods include electroporation, calcium phosphate-mediated transfection and DEAE-dextrane transfection. After transfection the cells are subjected to selection by treatment with a suitable agent based on the selection marker(s) encoded by the expression vector(s) to identify the stably transfected cells which contain the recombinant nucleic acid molecule.

The terms "medium", "cell culture medium" and "culture medium" are inter-changeably used herein and refer to a solution containing nutrients which are required for growing mammalian cells. Typically, a cell culture medium provides essential and non-essential amino acids, vitamins, energy sources, lipids, and trace elements required by the cell for minimal growth and/or survival. Preferably, the medium is chemically defined in that all its components and their concentration are known. Also preferably, the medium is serum-free and hydrolysate-free and does not contain any components derived from animals. Also preferably, the medium is serum-free and hydrolysate-free and does not contain yeast extract. In a more preferred embodiment the medium is serum-free and hydrolysate-free and does not contain any components derived from animals, insulin or L-glutamine. In a further more preferred embodiment the medium is serum-free and hydrolysate-free and does not contain any components derived from animals, insulin or L-glutamine, but contains poloxamer 188. "Hydrolysate-free" means that the medium does not contain a hydrolysate from plants which is prepared by hydrolyzing plant components to provide free amino acids, small peptides, carbohydrates and vitamins. In particular, the cell culture medium used in the present invention does not contain a soy hydrolysate and/or a cotton seed hydrolysate. If the cells are cultured in fed-batch mode as described below, the term "culture medium" refers to both the basal medium and the feed medium, unless stated otherwise.

In a particularly preferred embodiment the medium used in the method of the present invention is PolCHO P Powder Base CD, ActiPro (both available from GE), PowerCHO-2, ProCHO-5 (both available from Lonza) or Excell Advanced CHO (available from Sigma).

For culturing the mammalian cells different strategies are available, including batch culture, perfusion culture, continuous culture and fed-batch culture. Within the method of the present invention, preferably a fed-batch culture process is used. In fed-batch culture the culturing process is started with a certain volume of the basal medium and one or more feed media comprising one or more nutrients are fed at later time-point(s) of the culture process to prevent nutrient depletion while no product is removed from the cell culture broth.

The term "basal medium" is intended to refer to the medium which is used from the beginning of the cell culture process. The mammalian cells are inoculated into the basal medium and grown in this medium for a certain period until the feeding is started. The basal medium meets the definition of the culture medium as provided above.

The feed medium is added to the cell culture after the cells have been cultured in the basal medium for a certain period. The feed medium serves to prevent nutrient depletion and therefore may not have the same composition as the basal medium. In particular, the concentration of one or more nutrients may be higher in the feed medium than in the basal medium. In one embodiment, the feed medium has the same composition as the basal medium. In another embodiment, the feed medium has another composition as the basal medium. The feed medium may be added continuously or as a bolus at defined time points.

Suitable feed media are known to the skilled person and include PolCHO Feed-A Powder Base CD, PolCHO Feed-B Powder Base CD, Cell Boost 7a and Cell Boost 7b (all available from GE), BalanCD® CHO Feed 3 Medium (available from Irvine Scientific).

If PolCHO P Powder Base CD is used as basal medium, preferably PolCHO Feed-A Powder Base CD and/or PolCHO Feed-B Powder Base CD are used as feed medium. If Actipro is used as basal medium, preferably Cell Boost 7a and/or Cell Boost 7b are used as feed medium.

A certain amount of citrulline may be present in the basal medium and/or the feed medium, if it is present as a component of the medium, preferably the chemically defined medium, used. However, in one embodiment the amount of citrulline possibly present in the basal medium does not contribute to the amounts of citrulline provided herein as the amounts to be used in the methods of the present invention. In this embodiment, the amount of citrulline provided refers to the amount of citrulline added to the cell culture medium separately and intentionally.

The cell culture medium is preferably subjected to sterile filtration, more preferably to sterile filtration using a filter with 0.1 micron pore size.

As discussed above, in the methods of the present invention the cell culture medium comprises citrulline.

Citrulline is a non-proteinogenic amino acid having the following structure:

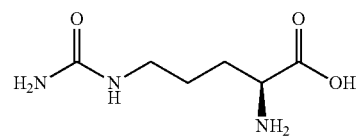 [SMILES: NC(=O)NCCC[C@H](N)C(=O)O]

Citrulline can for example be obtained from Sigma (Catalogue No. C7629-100G).

Cell culture media containing citrulline have been described in the prior art (see, e.g., WO 2010/036767 A1 and U.S. Pat. No. 5,045,468), but not in the context of reducing the amount of acidic species, increasing the amount of basic species, increasing cell size or increasing the specific production rate as described herein.

The term "citrulline" is intended to include also salts of citrulline such as L-citrulline DL-malate and oligomers and polymers of L-citrulline such as poly-L-citrulline. Preferably, the term "citrulline" refers to L-citrulline.

The cell culture medium comprises 2 to 30 g/l citrulline, preferably 3 to 20 g/l, more preferably 4 to 15 g/l citrulline, and most preferably 5 to 12 g/l citrulline. In certain embodiments, the cell culture medium comprises 5 g/l citrulline, 8 g/l citrulline or 12 g/l citrulline.

If the recombinant protein is ustekinumab or natalizumab, the cell culture medium preferably comprises 12 g/l citrulline.

Accordingly, the present invention also relates to a method of producing a composition comprising ustekinumab or natalizumab in Chinese Hamster Ovary cells expressing ustekinumab or natalizumab, the method comprising:

(a) culturing said cells in a cell culture medium comprising 12 g/l citrulline; and (b) obtaining the composition comprising ustekinumab from the cell culture medium.

In the methods of the present invention the citrulline may be present in both the basal medium and the feed medium in any of the concentrations provided above. In one embodiment the concentration of citrulline in the feed medium is the same as in the basal medium.

Alternatively, the citrulline may only be present in the basal medium, but not in the feed medium. In still another embodiment the citrulline is not present in the basal medium, but is only provided with the feed medium. In this later case, the concentration of citrulline in the feed medium may be higher than 30 g/l, for example in the range of 40 to 60 g/l and will be diluted in the culture medium to a concentration of 2 to 30 g/l, preferably of 3 to 20 g/l, more preferably of 4 to 15 g/l citrulline, and most preferably of 5 to 12 g/l citrulline.

Also preferably the citrulline is added to the cell culture medium, meaning that the citrulline is added as a separate component to the cell culture medium, preferably the basal medium and the feed medium, in any of the concentrations provided above. However, this does not exclude that either the basal medium or the feed medium or both comprises citrulline. However, if citrulline is present in either the basal medium or the feed medium or both, the concentration of citrulline in either the basal medium or the feed medium or both does not contribute to the concentrations provided above.

In one embodiment, the citrulline is added to the liquid cell culture medium. In one embodiment, the citrulline is added to the liquid cell culture medium as a powder. In one embodiment, the citrulline is added to the liquid basal medium. In one embodiment, the citrulline is added to the liquid basal medium as a powder. In one embodiment, the citrulline is added to the liquid feed medium. In one embodiment, the citrulline is added to the liquid feed medium as a powder. In one embodiment, the citrulline is added to the liquid basal medium and the liquid feed medium. In one embodiment, the citrulline is added to the liquid basal medium and the liquid feed medium as a powder.

In one embodiment of the methods of the present invention no lysine is added to the cell culture medium. This means that no extra amount of lysine is added to the cell culture medium, but does not exclude that lysine is present in the cell culture as one component of the cell culture medium, such as the basal medium or the feed medium. It was surprisingly found by the present inventors that the combined addition of citrulline and lysine to the cell culture medium has a stronger negative influence on viable cell density and product titer than the addition of citrulline alone.

In one embodiment of the methods of the present invention no arginine, histidine, ornithine or lysine is added to the cell culture medium. This means that no extra amount of arginine, histidine, ornithine or lysine is added to the cell culture medium, but does not exclude that any or all of arginine, histidine, ornithine or lysine is present in the cell culture as one component of the cell culture medium, such as the basal medium or the feed medium. In a particular embodiment of the methods of the present invention none of arginine, histidine, ornithine and lysine is added to the cell culture medium.

In one embodiment of the methods of the present invention no putrescine or derivative thereof, no spermidine or derivative thereof, no spermine or derivative thereof, no agmatine or derivative thereof and/or no cadaverine or derivative thereof is added to the cell culture medium.

In one embodiment the cell culture medium does not comprise putrescine or a derivative thereof, spermidine or a derivative thereof, spermine or a derivative thereof, agmatine or a derivative thereof and/or cadaverine or a derivative thereof.

In one embodiment the cell culture medium does not comprise any of putrescine or a derivative thereof, spermidine or a derivative thereof, spermine or a derivative thereof, agmatine or a derivative thereof and cadaverine or a derivative thereof.

In one embodiment of the methods of the present invention the temperature is changed during the culture process from a first temperature to a second temperature, i.e. the temperature is actively downregulated. Preferably, the second temperature is lower than the first temperature. The first temperature may be 37° C.±0.2° C. The second temperature may be in the range of from 25° C. to 36° C., preferably it is in the range of 28° C. to 36° C., more preferably it is in the range of 30° C. to 36° C., even more preferably it is in the range of 31° C. to 35° C. The second temperature may be 31° C., 33° C. or 35° C.

In one embodiment the first temperature is 37° C. and the second temperature is 31° C. In another embodiment, the first temperature is 37° C. and the second temperature is 33° C. In still another embodiment, the temperature the first temperature is 37° C. and the second temperature is 35° C.

The temperature is changed from the first temperature to the second temperature on day 3 to 7 after inoculation of the cell culture medium with the mammalian cells producing the recombinant protein. Preferably, the temperature is changed from the first temperature to the second temperature on day 4 to 6 after inoculation of the cell culture medium with the mammalian cells producing the recombinant protein. More preferably, the temperature is changed from the first temperature to the second temperature on day 5 after inoculation of the cell culture medium with the mammalian cells producing the recombinant protein. In one embodiment the cells are cultured at the second temperature for the rest of the culture period, i.e. the second temperature is not changed anymore.

In one embodiment the pH of the cell culture medium remains constant, meaning that the pH is not actively up- or down-regulated in the process and that always the same preset pH is used. Nevertheless, minor variations of the pH may occur during the culturing process.

In another embodiment, the pH of the cell culture medium is reduced from a first pH to a second pH after the mammalian cells have been cultured for a certain period of time. The first pH is maintained in the range of 7.0 to 7.2, preferably at pH 7.0. The second pH may be 0.1 to 0.3 pH units lower than the first pH and preferably, the second pH is 0.2 pH units lower than the first pH. The second pH may be in the range of 6.7 to 7.1. The pH may be lowered by adding a suitable acid or $CO_2$ gas, preferably by adding $H_3PO_4$.

The pH is changed from the first pH to the second pH on any day between day 3 and day 8 after inoculation of the cell culture medium with the mammalian cells producing the recombinant protein. Preferably, the pH is changed from the first pH to the second pH on day 4 to 6 after inoculation of the cell culture medium with the mammalian cells producing the recombinant protein. More preferably, the pH is changed from the first pH to the second pH on day 5 after inoculation of the cell culture medium with the mammalian cells producing the recombinant protein. In one embodiment the cells are cultured at the second pH for the rest of the culture period, i.e. the second pH is not changed anymore.

In the process of the present invention the cells are cultured under aerobic conditions, i.e. a level of dissolved oxygen of 5% to 95%, preferably of 40%±10% or 60%±10%.

If foaming of the cell culture occurs, antifoam agent may be added to the culture at any time during the process of the present invention.

The term "inoculation of the cells into the cell culture medium" refers to the step of contacting the cells with the cell culture medium under conditions which are suitable for growth and proliferation of the cells. It does not refer to any pre-culture of the cells which aims at expanding the cells until a certain number of cells is obtained.

The present inventors have also found that by culturing the mammalian cells in a cell culture medium comprising citrulline and/or sucrose the size of the mammalian cells is increased. The increase in the size of the mammalian cells is compared to the size of mammalian cells cultured in a cell culture medium not comprising citrulline and/or sucrose.

The effect of citrulline and/or sucrose on cell size is not limited to mammalian cells, but also applies to other eukaryotic cells such as fungal cells or insect cells so that the method for increasing the cell size can also be performed with these cells. Fungal cells include both cells from a filamentous fungus such as those from the genera *Aspergillus, Myceliophthora, Neurospora, Trichoderma, Penicillium* and *Rhizopus* and yeast cells such as *Saccharomyces cerevisiae, Pichia pastoris, Hansenula polymoipha, Kluyveromyces lactic, Schizosaccharomyces pombe, Yarrowia lipolytica* and *Arxula adeninivorans*. Insect cells include Schneider 2 (S2) cells from the late embryonic stages of *Drosophila melanogaster* and Sf-9 cells from the pupal ovarian tissue of the fall armyworm *Spodoptera frugiperda*.

Further, the effect of citrulline and/or sucrose on cell size is not limited to mammalian cells expressing a recombinant protein, but is also applicable to other mammalian cells such as, but not limited to, stem cells, B cells, T cells, dendritic cells and NK cells.

The term "cell size" refers to either the diameter of the cell or the volume of the cell. Preferably, the cell volume is increased by culturing the mammalian cells in a cell culture medium comprising citrulline. The cell diameter can be determined automatically using a flow cytometer or a cell counter. The cell diameter can be used to calculate the cell volume by using the formula for calculating the volume of a sphere, i.e. $4/3\pi \times r^3$ wherein r refers to the radius, i.e. half of the diameter.

The cell size is increased by at least 5%, preferably by at least 8% and more preferably by at least 10% when the mammalian cells are cultured in a cell culture medium comprising citrulline compared to the cell size of mammalian cells not cultured in a cell culture medium comprising citrulline. The increase in cell size is proportional to the concentration of citrulline in the cell culture medium, meaning that the higher the concentration of citrulline in the cell culture medium, the higher the increase in cell size. The increase in cell size is preferably determined ten to 14 days after inoculating the cells into the cell culture medium.

An additional finding of the inventors is that the specific production rate of mammalian cells expressing a recombinant protein is increased when the cells are cultured in a cell culture medium comprising citrulline compared to the specific production rate of said mammalian cells cultured in a cell culture medium not comprising citrulline. The increase in specific productivity raises considerable advantages for clarification and downstream processing.

The term "specific production rate" refers to the amount of recombinant protein produced per cell and day and is therefore given as pg cell$^{-1}$ day$^{-1}$. It can be calculated from the product titer and the integral viable cell concentration at a certain time point by the following formula:

$$Q_{p,i}=P_i/\text{cum IVCC}_i \text{ wherein:}$$

$Q_p$, is the average cell specific productivity (pcd: pg/cell/day) over the course of the run up to t=i
$P_i$ is the product titer (mg/l) at t=i
cum IVCC$_i$ is the cumulative IVCC at t=i
The cum IVCC$_i$ is calculated from the viable cell concentration and the culture age using the following formula:
IVCC$_i$=(vc$_i$+vc$_{i-1}$)*0.5*(D$_i$–D$_{i-1}$), wherein
IVCC$_i$ is the integral viable cell concentration (cells*days/ml) at time i
D$_i$ is the culture age (day) at time i
D$_{i-1}$ is the culture age (day) at time i–1
Vc$_i$ is the viable cell concentration (cells/ml) at time i
Vc$_{i-1}$ is the viable cell concentration (cells/ml) at time i–1
cum IVCC$_i$=cum IVCC$_{i-1}$+IVCC$_i$ The viable cell concentration can be determined automatically, e.g. using a cell counter such as the LUNA™ counter. The product titer can for example be determined by a spectrometer such as Octet QK.

The specific production rate is increased by at least 5%, preferably by at least 8% and more preferably by at least 10% and even more preferably by at least 12% when the mammalian cells are cultured in a cell culture medium comprising citrulline compared to the specific production rate of mammalian cells not cultured in a cell culture medium comprising citrulline. The increase in specific production rate is proportional to the concentration of citrulline in the cell culture medium, meaning that the higher the concentration of citrulline in the cell culture medium, the higher the increase in specific production rate. The increase in specific production rate is preferably determined ten to 14 days after inoculating the cells into the cell culture medium.

Still another finding of the inventors is that the apoptosis of mammalian cells is decreased, if the cells are cultured in a medium comprising citrulline and/or sucrose. One indicator for apoptosis is the activity of caspases. Caspases 3 and 7 are able to cleave and activate Xrp8 protein, which acts as a lipid scramblase and leads to the loss of membrane lipid asymmetry, resulting in phosphatidylserine exposure from the inner the to outer cell membrane (Marino et al. Cell Res 2013; 23: 1247-1248). Hence, activation of caspases 3 and 7 is considered as one of the first events of apoptosis followed by outer membrane phosphatidylserine expression. The activity of caspases 3 and 7 can be determined using a commercially available reagent such as the Caspase-Glo® 3/7 reagent of Promega.

The apoptosis of mammalian cells, as measured by determining the activity of caspases 3 and 7, is decreased by at least 7%, preferably by at least 12% and more preferably by at least 15% when the mammalian cells are cultured in a cell culture medium comprising citrulline and/or sucrose compared to the apoptosis of mammalian cells not cultured in a cell culture medium comprising citrulline and/or sucrose.

It was also found that the cell size and the specific production rate of mammalian cells expressing a recombinant protein can be further increased compared to the cell size and the specific production rate of mammalian cells expressing said recombinant protein and cultured in a medium comprising citrulline, if the cell culture medium comprises both citrulline and sucrose. A certain amount of citrulline and/or sucrose may be present in the basal medium and/or the feed medium, if they are present as components of the medium, preferably the chemically defined medium, used. However, in one embodiment the amount of citrulline and/or sucrose possibly present in the basal medium does not contribute to the amounts of citrulline and/or sucrose provided herein as the amounts to be used in the method of the present invention. In this embodiment the amount of citrulline and/or sucrose provided refers to the amount of citrulline and/or sucrose added to the medium separately and intentionally.

The cell culture medium comprises 5 to 80 mM sucrose, preferably 7 to 70 mM sucrose, more preferably 8 to 60 mM sucrose and most preferably 10 to 50 mM sucrose. The cell culture medium comprises 10 mM sucrose, 20 mM sucrose, 30 mM sucrose, 40 mM sucrose or 50 mM sucrose.

In the methods of the present invention the sucrose may be present in both the basal medium and the feed medium in any of the concentrations provided above. In one embodiment the concentration of sucrose in the feed medium is the same as in the basal medium.

Alternatively, the sucrose may only be present in the basal medium, but not in the feed medium. In still another embodiment the sucrose is not present in the basal medium, but is only provided with the feed medium.

The cell culture medium comprises 2 to 30 g/l citrulline and 5 to 80 mM sucrose, preferably 3 to 20 g/l citrulline and 7 to 70 mM sucrose, more preferably 4 to 15 g/l citrulline and 8 to 60 mM sucrose, and most preferably 4 to 12 g/l citrulline and 10 to 50 mM sucrose. In certain embodiments, the cell culture medium comprises 4 g/l citrulline and 10 mM, 20 mM, 30 mM, 40 mM or 50 mM sucrose. In certain embodiments, the cell culture medium comprises 8 g/l citrulline and 10 mM, 20 mM, 30 mM, 40 mM or 50 mM sucrose. In certain embodiments, the cell culture medium comprises 12 g/l citrulline and 10 mM, 20 mM, 30 mM, 40 mM or 50 mM sucrose.

In the methods of the present invention the citrulline and the sucrose may be present in both the basal medium and the feed medium in any of the concentrations provided above. In one embodiment the concentration of citrulline and sucrose in the feed medium is the same as in the basal medium.

Alternatively, the citrulline and sucrose may only be present in the basal medium, but not in the feed medium. In still another embodiment the citrulline and sucrose are not present in the basal medium, but are only provided with the feed medium.

The cell size is increased by at least 5%, preferably by at least 8% and more preferably by at least 10% when the mammalian cells are cultured in a cell culture medium comprising citrulline and sucrose compared to the cell size of mammalian cells not cultured in a cell culture medium comprising citrulline and sucrose. The increase in cell size is proportional to the combined concentration of citrulline and sucrose in the cell culture medium, meaning that the higher the combined concentration of citrulline and sucrose in the cell culture medium, the higher the increase in cell size. The increase in cell size is preferably determined ten to 14 days after inoculating the cells into the cell culture medium.

The specific production rate is increased by at least 8%, preferably by at least 10% and more preferably by at least 12% and even more preferably by at least 15% when the mammalian cells are cultured in a cell culture medium comprising citrulline and sucrose compared to the specific production rate of mammalian cells not cultured in a cell culture medium comprising citrulline and sucrose. The increase in specific production rate is proportional to the combined concentration of citrulline and sucrose in the cell culture medium, meaning that the higher the combined concentration of citrulline and sucrose in the cell culture medium, the higher the increase in specific production rate. The increase in specific production rate is preferably determined ten to 14 days after inoculating the cells into the cell culture medium.

After the recombinant protein has been produced according to any of the methods of the present invention for producing a recombinant protein, the recombinant protein is harvested from the cell culture. Since recombinant proteins, in particular antibodies, expressed from mammalian cells are typically secreted into the cell culture fluid during the cultivation process, the product harvest at the end of the cultivation process occurs by separating cell culture fluid comprising the recombinant protein from the cells. The cell separation method should be gentle to minimize cell disruption to avoid the increase of cell debris and release of proteases and other molecules that could affect the quality of the recombinant protein product. Usually, the harvesting of the cell culture fluid comprising the recombinant protein involves centrifugation and/or filtration, whereby the recombinant protein is present in the supernatant and the filtrate, respectively. Expanded bed adsorption chromatography is an alternative method to avoid centrifugation/filtration methods.

In one embodiment the harvesting of the cell culture fluid comprises depth filtration of the cell culture fluid. Depth filters use a porous medium to retain particles throughout the medium and not only on the surface of the medium. Suitable depth filters include Millistak+D0HC and C0HC filters.

It has been found that the methods of the present invention increase the filtration efficiency in the depth filtration of the cell culture fluid, as they increase the maximum capacity of the depth filter. The maximum capacity of the depth filter is defined as the weight of the monoclonal antibody which can be filtered per square meter of filter surface. The maximum capacity is increased by at least 10% or 15%, preferably by at least 20% or 25%, more preferably by at least 30% and most preferably by at least 35%, when a cell culture fluid obtained from a cell culture using a cell culture medium comprising citrulline and/or sucrose is used, compared to the filtration of a cell culture fluid obtained from a cell culture using a cell culture medium not comprising citrulline and/or sucrose.

The methods of the present invention also lead to a lower content of residual host cell protein in the depth filtrates when a cell culture fluid obtained from a cell culture using a cell culture medium comprising citrulline and/or sucrose is subjected to depth filtration compared to the residual host cell protein content, when a cell culture fluid obtained from a cell culture using a cell culture medium not comprising citrulline and/or sucrose is subjected to depth filtration. The host cell protein content can be determined by commercially available kits such as the CHO HCP ELISA kit 3G obtainable from Cygnus Technologies. The content of residual host cell proteins is decreased by at least 10%, preferably by at least or 15% or 20%, more preferably by at least 22% or 25%, and most preferably by at least 28% or 30%, if a cell culture fluid obtained from a cell culture using a cell culture medium comprising citrulline and/or sucrose is subjected to depth filtration compared to the residual host cell protein content, when a cell culture fluid obtained from a cell culture using a cell culture medium not comprising citrulline and/or sucrose is subjected to depth filtration.

After harvesting the cell culture fluid comprising the recombinant protein the recombinant protein has to be purified from the cell culture fluid. The purification of recombinant proteins and in particular recombinant antibodies is usually accomplished by a series of standard techniques that can include chromatographic steps such as anion exchange chromatography, cation exchange chromatography, affinity chromatography, hydrophobic interaction chromatography, hydroxyapatite chromatography and size exclusion chromatography. Further, the purification process may comprise one or more ultra-, nano- or diafiltration steps.

Within the present invention the terms "obtaining the composition comprising the antibody" or "obtaining the composition comprising the recombinant protein" are intended to refer to the steps of harvesting the cell culture fluid and purifying the recombinant protein or antibody.

After purifying the recombinant protein it can be used to prepare a pharmaceutical composition. A pharmaceutical composition is a composition which is intended to be delivered to a patient for treating or preventing a disease or condition. In addition to the active agent, i.e. the recombinant protein, a pharmaceutical composition typically contains at least one pharmaceutically acceptable excipient. Pharmaceutically acceptable excipients are substances which do not interfere with the physiological activity of the recombinant protein and which stabilize the pharmaceutical composition and/or enhance solubility or decrease viscosity of the pharmaceutical composition. Typical pharmaceutically acceptable excipients for monoclonal antibodies include buffers, salts, sugars or sugar alcohols, amino acids and surface-active agents.

The process of the present invention improves the biosimilarity of a biosimilar therapeutic antibody to its reference product, i.e. the marketed therapeutic antibody. A biosimilar therapeutic antibody is a therapeutic antibody which is marketed after the patent protection for the original product has expired and which has the same amino acid sequence as the original product, but may slightly differ in posttranslational modifications. Nevertheless, they show a physiological effect which is identical to that of the original product. When an application for a marketing authorization for a biosimilar of a marketed antibody is filed, it has to be shown that the structure of the biosimilar antibody is comparable to the reference product.

By using the methods of the present invention the amount of acidic and basic species of the biosimilar antibody is comparable to that of the reference product, thereby improving the bio similarity compared to an antibody which has been produced in a cell culture medium not comprising citrulline.

The following examples and figures are provided for illustrative purposes. It is thus understood that the examples and figures are not to be construed as limiting. The skilled person in the art will clearly be able to envisage further modifications of the principles laid out herein.

EXAMPLES

The method of the present invention is supported and illustrated by reference to the following non-limiting examples.

The selected experiments presented below were performed with ustekinumab, a human anti-p40, IgG1 antibody, which was recombinantly expressed in CHO-K1 cells propagated in fed-batch cultures of different scales. Further sets of experiments were performed with the antibodies natalizumab and omalizumab which demonstrate that the effects observed with ustekinumab are not specific to this antibody.

Hence, the invented methods do neither depend on specific antibodies nor on specific host cells used for the expression of the immunoglobulins. The same is true for the mode of expression and the selected culture conditions.

1. Methods 1.1 Cell Lines and Culture Conditions 1.1.1 Stirred Tank Reactor Experiments with Cells Expressing Ustekinumab Cell lines C20 and C69 expressing the biosimilar recombinant monoclonal antibody ustekinumab were used in the stirred tank reactor experiments.

The stirred tank reactors (STRs) were inoculated with the cell line C20 or with the cell line C69 in pre-heated production medium (PolCHO-P, available from GE healthcare, Catalogue Number G3258.3050), at a target density of $1.0*10^6$ viable cells (vc) $mL^{-1}$. From day 3 on, 4.2% (v/v) of feed A (available from GE healthcare, Catalogue Number G3259.3010) per day was added at a continuous rate over 24 hours (equivalent to 2.9 g glucose $L^{-1}$ $day^{-1}$). If required, a D-glucose solution was used to increase glucose concentration in the broth to 4 g $L^{-1}$. In addition, 0.42% (v/v) of feed B (available from GE healthcare, Catalogue Number G3260.0001) was added every day as a bolus. For cell line C20 different concentrations of citrulline (5 g/l, 8 g/l and 12 g/l) were added to the medium and to feed A. For cell line C69 10 g/l citrulline in combination with 40 mM sucrose were added to the medium and to feed A.

Dissolved oxygen concentration (DO) was controlled at 40% air saturation. Stirring speed and gasflow through a macrosparger were started at 200 rpm and 0.04 L $min^{-1}$, respectively. During the course of the fed-batch, stirring speed and gasflow rate were increased manually to increase oxygen transfer capacity of the system. Headspace aeration was constant at 0.05 L $min^{-1}$. pH was kept below set-point with a one-way pH control using $CO_2$ addition. If required, antifoam was added manually. Cultures were kept in the dark by covering the STRs in order to prevent oxidation of the product. The operating conditions are summarized in Table 1. At day 5 after inoculating the cells into the cell culture medium the temperature of the cell culture was reduced to 31° C.±0.2° C.

TABLE 1

| Operating conditions of STRs | |
|---|---|
| Operational parameter | Set-point |
| Inoculation density | $1.0*10^6$ vc $mL^{-1}$ ± $0.2*10^6$ vc $mL^{-1}$ |
| Culture start volume | 1200 mL ± 50 mL |
| Temperature | 37° C. ± 0.2° C. |
| pH | 7.0 ± 0.1 |
| Dissolved oxygen (DO) | 40% ± 10% |
| Agitation | 200 rpm |
| Sparger flow rate | 0.04 L $min^{-1}$ |
| Headspace aeration | 0.05 L $min^{-1}$ |
| Antifoam addition | If required | pH, DO, temperature, gas flow and agitation rates were measured online with the help of the Iris software of Infors HT. In addition, samples were taken daily to monitor viable cell density, cell viability and average cell diameter using a Luna™ automated cell counter according to manufacturer's instructions. Glucose and lactate concentrations in the culture were determined using a Biosen S-line analyzer. Approximately 0.5 mL of the samples was centrifuged to remove cell debris and supernatant was stored at −20° C. for titer determination with an Octet QK using protein A biosensors.

Additional samples of approximately 30 mL were collected on days 6, 10 and 14, centrifuged and stored in −80° C. for product quality analysis. For the experiments with cell line C69 samples were also taken to determine the concentration of citrulline at different time points (days 8, 11, 13 and 14) during the bioreactor run.

1.1.2 Shake Flask Experiments with Cells Expressing Ustekinumab a) Cell line C367 expressing the biosimilar recombinant monoclonal antibody ustekinumab was used in the shake flask experiments.

The shake flasks were inoculated in 25 mL Actipro medium (available from GE healthcare, Catalogue number SH31039.01) and placed on a shaking plateau in an incubator at 37° C. On the day of inoculation, 2% (v/v) of Cell boost 7A (available from GE healthcare, Catalogue number SH31026.02) and 0.2% (v/v) of Cell boost 7B (available from GE healthcare, Catalogue number SH31027.01) was given. From day 3 on, a flat feed was given of 4% (v/v) of Cell boost per day. Every day before feeding, glucose concentration was measured. If required, a D-glucose solution was used to increase glucose concentration in the broth to 4 g $L^{-1}$, before feeding. In addition, 0.4% (v/v) of Cell boost 7B was added every day as a bolus. Different concentrations of citrulline (5 g/l and 8 g/l) were added to the medium and to Cell boost 7A. At day 5 after inoculating the cells into the cell culture medium the temperature of the cell culture was reduced to 31° C.±0.2° C.

Samples were taken daily to monitor viable cell density, cell viability and average cell diameter using a Luna™ automated cell counter. Glucose and lactate concentrations in the culture were determined using a Biosen S-line analyzer. Approximately 0.5 mL of the samples was centrifuged to remove cell debris and supernatant was stored at −20° C. for titer determination with an Octet QK using protein A biosensors.

On day 14, or when viability dropped below 30%, cultures were stopped, centrifuged and stored in −80° C. for product quality analysis.

b) In another set of experiments cell line C20 expressing ustekinumab was selected. This cell line was thawed and cultured in 25 mL shake flasks (SFs) containing PolCHO-P CD (GE Healthcare) medium with methotrexate and geneticin. Subsequently, the cells were expanded in SFs with increasing volume as seed train. Two passages before the experiment selection (methotrexate and geneticin) was released. 12 SFs were inoculated at a concentration of 0.5·$10^6$ vc $mL^{-1}$. The SFs were inoculated in 25 mL PolCHO-P CD medium and placed on a shaking plateau in an incubator at 37° C. On the day of inoculation 2% (v/v) of PolCHO feed A (GE Healthcare) and 0.2% (v/v) of PolCHO feed B (GE Healthcare) was given. From day 3 on, a flat feed was given of 4% (v/v) of PolCHO feed A per day. Every day before feeding, glucose concentration was measured. If required, a D-glucose solution was used to increase glucose concentration in the broth to 4 g $L^{-1}$, before feeding. In addition, 0.4% (v/v) of PolCHO feed B was added every day as a bolus. Different concentrations of citrulline and sucrose were added to the medium and to PolCHO feed A.

c) Bioreactor experiments with cells expressing natalizumab

Cell lineC4 expressing natalizumab was cultured in 15 ml AMBR microbioreactors. Dissolved oxygen tension (DOT) was controlled at 40% and the temperature maintained at 36.8° C. during the first 4 days with a temperature shift to 33° C. on day 5 for the rest of the cultivation time. The targeted viable cell concentration at inoculation was 1.0× $10^6$±0.1 viable cells $mL^{-1}$. The post inoculation volume of the production stage bioreactors was set to 15 mL in the microbioreactors of the AMBR system. The pH set point was 7.0±0.1. The basal medium was PolCHO-P CD (available from GE healthcare). From day 3 on, 4.2% (v/v) of PolCHO feed A (available from GE healthcare) per day was added as a bolus. If required, a D-glucose solution was used to increase glucose concentration in the broth to 4 g $L^{-1}$. In addition, 0.42% (v/v) of PolCHO feed B (available from GE healthcare) was added every day as a bolus. Different concentrations of citrulline were added to the medium. Samples were collected on day 14 to determine charged variants.

d) Shake flask experiments with cells expressing omalizumab

CHO cell line 230×846 expressing the anti-IgE antibody omalizumab was selected for this experiment. The cell line was thawed and cultured in 25 mL shake flasks (SFs) containing PowerCHO-2 CD medium (Lonza) with 4 mM L-glutamine and 1% (v/v) Fe-citrate solution. Subsequently, the cells were expanded in SFs with increasing volume as seed train. 12 SFs were inoculated at a concentration of 0.5·$10^6$ vc $mL^{-1}$. The SFs were inoculated in 25 mL PowerCHO-2-CD medium containing L-glutamine and Fe-citrate and placed on a shaking plateau in an incubator at 37° C. On the day of inoculation, 2% (v/v) of BC feed and 0.2% (v/v) of cys/tyr feed was given. The glucose concentration was measured every day before feeding. From day 3 on, feeding was done based on glucose consumption of the previous day, aiming for a glucose concentration of 3.5 g/L. Different concentrations of citrulline were added to the medium and BC feed.

1.2 Antibody Purification

The antibodies were purified using Protein A HP MultiTrap from GE healthcare (cat no. 28-9031-33) according to the following procedure:

Collection cluster tubes for eluted fractions, each containing 30 µl neutralizing buffer (1 M Tris-HCl pH 9.0) per tube, were prepared. The Protein A beads were suspended gently by shaking the plate upside down. The top and bottom seals were removed and the MultiTrap plate was placed on a collection plate. The storage solution was removed by vacuum (0.15 bar) until the wells were empty, then the vacuum was slowly increased to 0.3 bar. The MultiTrap plate was pre-equilibrated by applying 300 µl of Buffer H (0.02 M sodium phosphate, 0.15 M NaCl pH 7.4) and briefly mixed. A total of 0.75 mg of antibody was applied and the plate was incubated for 10 minutes while mixing and then vacuum was applied. 300 µl of Buffer I (0.02 M sodium phosphate, 1 M NaCl pH 7.4) were applied and briefly mixed and then vacuum was applied. Then 300 µl of Buffer H were applied, briefly mixed and vacuum was applied. This step was repeated once. The antibody was eluted by applying 200 µl of elution buffer (20 mM CH$_3$COOH, 40 mM NaCl pH 3.2), mixing, and vacuum collecting the eluate in the collection tube. This elution step was repeated once and the eluate was collected in the same collection tube.

1.3 Cation Exchange Chromatography a) of ustekinumab

The separation of acidic, main and basic peaks was performed with both a weak and a strong cation exchange resin.

The weak cation exchange resin used was ProPac WCX-10 (Cat. No. 054993, Thermo Scientific) with the following buffers:
Buffer A: 25 mM sodium phosphate monobasic
Buffer B: 25 mM sodium phosphate dibasic
Buffer C: 150 mM sodium chloride
Buffer D: 2.5 M sodium chloride
The gradient applied was as follows:

| Time (min) | Flow rate (ml/min) | Buffer A (%) | Buffer B (%) | Buffer C (%) | Buffer D (%) | Curve |
|---|---|---|---|---|---|---|
| 0.00 | 0.500 | 35.6 | 44.4 | 20.0 | 0.0 | Initial |
| 3.00 | 0.500 | 35.6 | 44.4 | 20.0 | 0.0 | 6 |
| 25.00 | 0.500 | 16.0 | 64.0 | 20.0 | 0.0 | 6 |
| 30.00 | 0.500 | 8.8 | 71.2 | 20.0 | 0.0 | 6 |
| 31.00 | 0.500 | 0.0 | 0.0 | 0.0 | 100.0 | 6 |
| 36.00 | 0.500 | 0.0 | 0.0 | 0.0 | 100.0 | 6 |
| 37.00 | 0.500 | 35.6 | 44.4 | 20.0 | 0.0 | 6 |
| 45.00 | 0.500 | 35.6 | 44.4 | 20.0 | 0.0 | 6 |

The strong cation exchange resin used was Proteomix SCX-NP1.7 (Cat no.: 401NP2-4615, Sepax) with the following buffers:
Buffer A: 4.8 mM Tris, 3 mM imidazole, 23.2 mM piperazine, pH 6.0
Buffer B: 4.8 mM Tris, 3 mM imidazole, 23.2 mM piperazine, pH 9.5
Buffer C: 200 mM sodium chloride
Buffer D: water
The gradient applied was as follows:

| Time (min) | Flow rate (ml/min) | Buffer A (%) | Buffer B (%) | Buffer C (%) | Buffer D (%) | Curve |
|---|---|---|---|---|---|---|
| 0.00 | 0.350 | 50.0 | 0.0 | 42.5 | 7.5 | Initial |
| 3.00 | 0.350 | 50.0 | 0.0 | 42.5 | 7.5 | 6 |
| 35.00 | 0.350 | 22.5 | 27.5 | 50.0 | 0.0 | 6 |
| 36.00 | 0.350 | 0.0 | 50.0 | 50.0 | 0.0 | 6 |
| 40.00 | 0.350 | 0.0 | 50.0 | 50.0 | 0.0 | 6 |
| 50.00 | 0.350 | 50.0 | 0.0 | 42.5 | 7.5 | 1 |

The column temperature was 40° C. and elution was monitored at 280 nm.

For data evaluation the Waters Empower 3 software was used. The sample composition was determined by detecting peaks based on their retention time and the relative proportions of each peak were calculated from the peak areas. The final results were presented as a sum of acidic species, main peak and sum of basic species.

b) of natalizumab

The separation was carried out by Cation Exchange High Performance Liquid Chromatography on the UPLC H-Class Bio System using UV detection under Empower™ Software control. The Waters Protein-Pak Hi Res SP (7 µm, 4.6 mm i.d.×100 mm) was used for testing applying a linear gradient of NaCl. Eluents were: buffer A (14 mM NaPi buffer pH 6.0) and buffer B (10.5 mM NaPi buffer pH 6.0, 0.125 M NaCl). The gradient started with pre-equilibration of 100% buffer A in 5 min. The elution gradient started from 10% to 30% of buffer B in 25 minutes, followed by a washing step for 5 min at 30% B and re-equilibration with 90% solvent A. The total run time was 45 min. The flow rate was 0.7 ml/min. The column temperature was 40° C. and elution was monitored at 220 nm.

For data evaluation the Waters Empower 3 software was used. The sample composition was determined by detecting peaks based on their retention time and the relative proportions of each peak were calculated from the peak areas. The final results were presented as a sum of acidic species, main peak and sum of basic species.

1.4 N-Glycan Analysis

The N-glycan composition and relative distribution thereof was analyzed using the Rapifluor MS N-Glycan Kit purchased from Waters, using the manufacturer's instructions. It comprises denaturation and release of N-linked glycans by PNGase F from Protein A purified material. The released glycans are then labeled with the proprietary Rapifluor label, which contains a fluorescent moiety and a proton capturing moiety. The released and labeled glycans are then captured by solid phase extraction and subsequently separated based on Hydrophilic Interaction Chromatography (HILIC). The retention time of each labeled Glycan is converted to a GU-value based on an external dextran standard ladder, which is subsequently matched to a library of known glycan structures. Besides retention time based matching, assignments of Glycans are further substantiated by their exact mass, that is also included in the reference library.

1.5 Determination of Viable Cell Concentration, Viability and Cell Size

The viable cell concentration, viability and cell size were determined using a LUNA™ cell counter with the following protocol:

A ~0.5 ml sample of a homogeneous cell suspension was taken and transferred to a 15 ml tube. 10 µl of Trypan blue stain were added to a round bottom well (96-wells plate). The 0.5 ml sample was scraped 3 times by firm strokes over a 15 ml tube rack to get rid of possible cell clumps. 10 µl of the sample were added to the 10 µl of Trypan blue stain and the resulting solution was mixed by gently resuspending the solution 5-10 times with a 15 µl pipette. 10 µl of the mixed cell sample were loaded into the inlet of a chamber of the counting slide. The LUNA™ counter determines total cell density, viable cell density, viability and cell diameter.

1.6 Determination of Antibody Titer and Specific Production Rate

The Octet system performs label-free quantitation of antibodies, proteins, peptides, DNA and other biomolecules and provides kinetic characterization of biomolecular binding interactions. The instrument provides rapid and accurate concentration data for antibodies and other proteins in crude lysates, untreated supernatants, and other complex samples and analyzes protein-protein interactions to provide kobs, ka, kd and KD information. Cell debris does not affect the measurement. The measurement range of the Octet system is ~0.50-40 µg/ml. The Octet instrument contains a high performance spectrometer and utilizes a label-free Biolayer Interferometry (BLI) technology to monitor real-time biomolecular interactions. The BLI technology is based on that any change in the number of molecules bound to the biosensor tip changes the optical layer thickness which causes a shift in the interference pattern. Adding molecules (binding) to the molecular layer increases the thickness of the biological layer and results in the interference pattern shifting to the right. Reducing the thickness of the layer (dissociation) shifts the wavelength peaks to the left. The binding rates of the test samples are measured and interpolated from a standard curve generated from a similar or equivalent protein to determine the concentration of the protein.

The specific production rate Qp was calculated from the product titer and the integral viable cell concentration at a certain time point by the following formula:

$$Q_{p,i} = P_i / \text{cum IVCC}_i \text{ wherein:}$$

$Q_{p,i}$ is the average cell specific productivity (pcd: pg/cell/day) over the course of the run up to t=i
$P_i$ is the product titer (mg/l) at t=i
cum $IVCC_i$ is the cumulative IVCC at t=i
The cum $IVCC_i$ was calculated from the viable cell concentration and the culture age using the following formula:

$$IVCC_i = (vc_i + vc_{i-1}) * 0.5 * (D_i - D_{i-1}), \text{ wherein}$$

$IVCC_i$ is the integral viable cell concentration (cells*days/ml) at time i
$D_i$ is the culture age (day) at time i
$D_{i-1}$ is the culture age (day) at time i−1
$Vc_i$ is the viable cell concentration (cells/ml) at time i
$Vc_{i-1}$ is the viable cell concentration (cells/ml) at time i−1
cum $IVCC_i$=cum $IVCC_{i-1}$+$IVCC_i$

1.7 Cell Culture Clarification by Depth Filtration and Maximum Filter Capacity Determination The cell culture to be harvested was connected by silicon tubing to a peristaltic pump with integrated pressure/weight recording software (KR2i, Spectrumlabs, Catalogue Number: 708-12202-000). Sterile single-use polysulfone pressure transducers (Spectrumlabs, Catalogue Number: ACMP-799-01N) were placed in front of the depth filter to monitor the pressure build-up during filtration. Two depth filters were tested for each cell culture, i.e. Millistak+® D0HC depth filter in POD® format (Merck, Catalogue Number: mD0HC23CL3) and Millistak+® C0HC depth filter in POD® format (Merck, Catalogue Number: mC0HC23CL3). The filter surface for both is 23 cm$^2$ and equilibration was carried out according to the supplier's manual.

The cell culture was gently stirred throughout filtration to assure a homogeneous cell suspension. Filtration was carried out at a flow rate of 150 liters per square meter and hour (LMH) until the pre-filter pressure reached 1 bar. The filtrate collection bottle was placed on a balance which is connected to the pump system for weight recording. The filtrate weight at 1 bar pressure was used for capacity calculation.

1.8 Turbidity Measurements

To evaluate the amount of non-soluble particles in a solution and thus the amount of cell (debris) retention during filtration, turbidity measurements are generally used. For turbidity measurements of (unclarified) cell cultures and (depth) filtrates, the portable turbidimeter 2100Qis (HACH, Catalogue Number: 2100QIS01) was used. This device contains a light-emitting diode (wavelength: 860 nm) as light source and a silicon photodiode detector. The measurement range is between 0-1000 formazin nephelometric units (FNU). In case the turbidity is above 1000 FNU, the sample needs to be diluted in phosphate buffered saline with neutral pH (PBS). Low FNU values indicate good cell (debris) retention and consequently a high quality filtration.

1.9 Determination of Residual Host Cell Protein Content by ELISA

To quantify residual amounts of soluble (CHO) host cell proteins (HCP) in depth filtrates, the widely used CHO HCP ELISA kit 3G (Cygnus Technologies, Catalogue Number: F550) is used. A standard curve using solutions of known CHO protein concentration (supplied with the kit) was prepared. To fall within the standard range, each filtrate was diluted 20,000 and 40,000 fold. HCP determination by the generic ELISA kit was carried out essentially as described in the supplier's manual. As a read-out the absorption at wavelengths of 450 and 655 nm was determined on a iMARK microplate reader (Biorad, Catalogue Number: 168-1130). The absorption values determined are correlated to a concentration value in ng HCP per mL sample by means of the standard curve. In order to calculate the residual HCP content in ppm (ng HCP per mg of monoclonal antibody), the monoclonal antibody concentration in the filtrates was determined by Octet according to section 1.6.

1.10 Determination of Citrulline Concentration in Culture Medium

To determine if citrulline can be metabolised by CHO cells clarified samples were taken from the stirred tank reactor run with clone C69. Quantification of the concentration of citrulline during the culture was standardized using a 10 g/l citrulline solution in WFI and the PolCHO medium was used as a negative control.

a) Sample Preparation
About 1 mL of culture medium was centrifuged in an Eppendorf centrifuge at 15000 rpm and at 4° C. for 10 minutes. For NMR analysis, 500 µL of medium supernatant was added to 50 µL of 10 mM TSP (3-(trimethylsilyl-)propionic-2,2,3,3-d4 acid sodium salt) in D2O, mixed and transferred to a 5-mm NMR tube.

A calibration curve was prepared for UPLC-MS analysis of citrulline by serial dilutions of the citrulline reference standard in water. Medium supernatants were diluted 1000-fold in water and transferred to well-plates for automated analysis by UPLC-MS.

b) 1H-NMR
$^1$H-NMR spectra were recorded on a Bruker 500 MHz Avance III system (Bruker Biospin, Rheinstetten, Germany) equipped with a 5-mm CryoProbe, CPTCI ($^1$H—$^{13}$C/$^{15}$N/$^2$H+Z-gradients). $^1$H-NMR spectra were recorded in quantitative mode at 303 K. Data were acquired and pre-processed with Topspin software version 2.1 (Bruker Biospin, Germany). NMR data analysis was performed using MestRenova 11 (Mestrelab Research S.L, Spain).

c) UPLC-MS
UPLC-QToF-MS measurements were performed on a Waters ACQUITY UPLC coupled to a Waters Xevo QToF mass spectrometer, using electrospray ionization in positive ion mode. The UPLC-MS system was equipped with a Binary Solvent Manager, an ACQUITY HSS T3 column, a PDA detector and a Sample Manager. Amino acid separation on the UPLC column was achieved by gradient elution with a mobile phase containing acetonitrile/water/HFBA/formic acid.

Data were acquired and processed using MassLynx V4.1 and QuanLynx V4.1 software by Waters.

Using reference sample, the molecular mass of citrulline was confirmed by UPLC-MS to be 175.08 Da. The concentration of citrulline in the reference sample was 55.84 mM as determined by qNMR. The citrulline concentrations in culture medium samples of days 8, 11, 13 and 14 were determined by UPLC-MS analysis after appropriate dilution of the samples and by using external calibration lines prepared using the reference sample. No citrulline was detected in POLCHO medium (see FIG. 11).

1.11 Determination of Caspase 3/7 Activity in CHO Cells

On day 11, control and 10 g/L L-citrulline/40 mM sucrose-treated CHO cells were harvested, and put at 0.2× $10^6$ cells/mL in PolCHO-P (available from GE healthcare) with 6 mM L-glucose, and then added to 96-wells flat-bottom white assay plates (Corning) at 0·0.2×$10^6$ cells/100 4/well. After this, 50 μl/well Caspase-Glo® 3/7 Reagent (Promega) was added these cells, and incubated for 60 minutes at RT, followed by measurement of caspase 3/7 activity using a luminometer (Biotek).

1.12 Determination of Outer Membrane Phosphatidylserine Expression Levels on CHO Cells On day 11, control and 10 g/L L-citrulline/40 mM sucrose-treated CHO cells were harvested, and put at 2.0× $10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma-Aldrich) for 10 minutes at 4° C. Then, 100 μL/tube (ie, 0.2×$10^6$ cells) of these cells were incubated with 10 μL mouse anti-phosphatidylserine antibody (Millipore) at 25 μg/mL (in PBS/BSA/$NaN_3$) for 30 minutes at 4° C. In parallel, 10 μL purified mouse IgG1 isotype control (BD Biosciences) at 25 μg/mL (in PBS/BSA/$NaN_3$) was run as a negative control. After extensive washing in PBS/BSA/$NaN_3$, cells were subsequently incubated with 1:200 diluted PE-conjugated goat anti-mouse IgG Fcγ-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Outer membrane phosphatidylserine expression levels (geo-mean fluorescence intensity) were measured using a flow cytometer (FACSCalibur; BD Biosciences).

1.13 Determination of Autophagy by Intracellular Autophagic Vacuole Expression Levels in CHO Cells On day 11, control and 10 g/L L-citrulline/40 mM sucrose-treated CHO cells were harvested, and put at 5.0× $10^6$ cells/250 μL in PBS/5% (v/v) FCS (Bodinco). Then, 250 μL of Green Detection Reagent (Autophagy Detection Kit; Abcam), a specific cationic amphiphilic tracer, was added to these cells, and the mixture was incubated for 30 minutes at RT. After washing the cells in Assay Buffer (Autophagy Detection Kit; Abcam), intracellular autophagic vacuole expression levels (geo-mean fluorescence intensity) were measured using a flow cytometer (FACSCalibur; BD Biosciences).

2. Results

2.1 Analysis of Acidic and Basic Species

Figure 1:
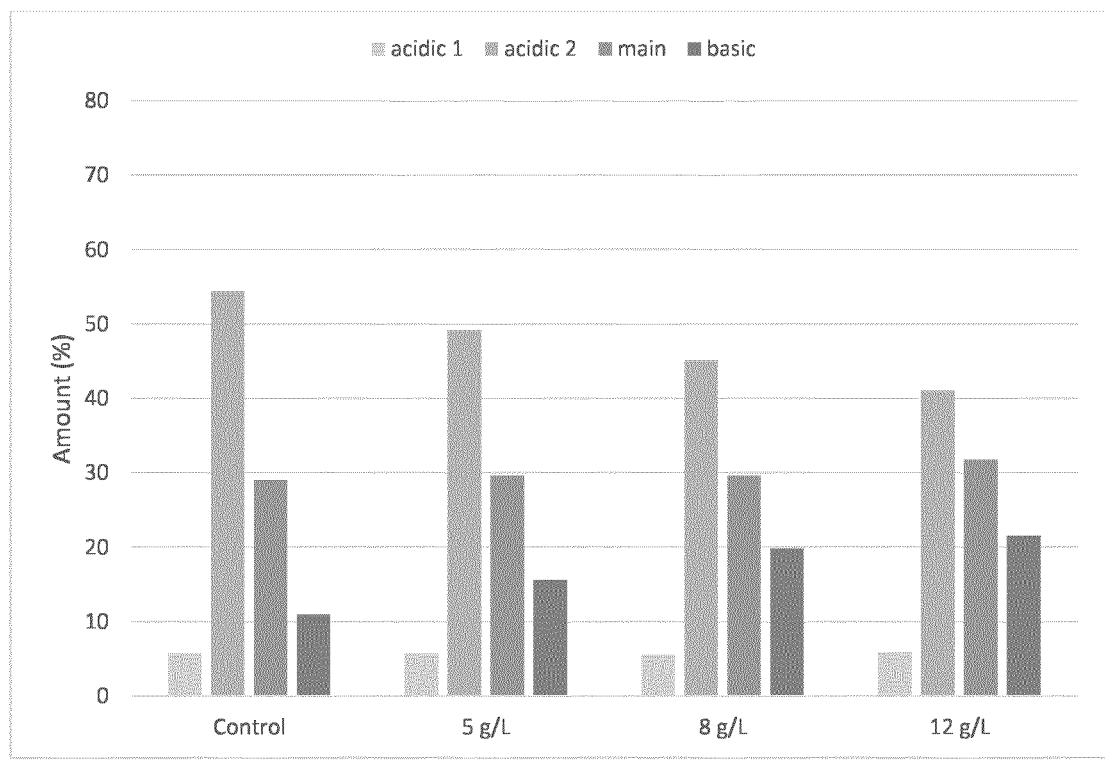
FIG. 1: Analysis of acidic species, main species and basic species in the ustekinumab antibody produced in CHO cells by cation exchange chromatography. The cells were cultured without citrulline (control), 5 g/l, 8 g/l and 12 g/l citrulline for 14 days. For each of the conditions, the bars show from left to right: acidic species 1, acidic species 2, main species and basic species.

The addition of citrulline to the cell culture medium affects charged variants of the monoclonal antibodies ustekinumab and natalizumab. In FIG. 1, data of a cation exchange chromatography analysis of the day 14 ustekinumab samples are shown. It can be seen that the acidic 2 peaks are decreased dose-dependently by increasing concentrations of citrulline. Further, basic peaks increase dose-dependently, from 11% in the control condition at day 14 to 22% in the condition with 12 g $L^{-1}$ citrulline. The same effect can also be observed after culturing the cells for 6 or 12 days in a cell culture medium containing citrulline (data not shown).

FIG. 7 shows for natalizumab that the sum of acidic peaks decreased dose-dependently by increasing concentrations of citrulline and that the sum of basic peaks increased dose-dependently by increasing concentrations of citrulline.

2.2 Analysis of Cell Size and Specific Production Rate

Figure 2:
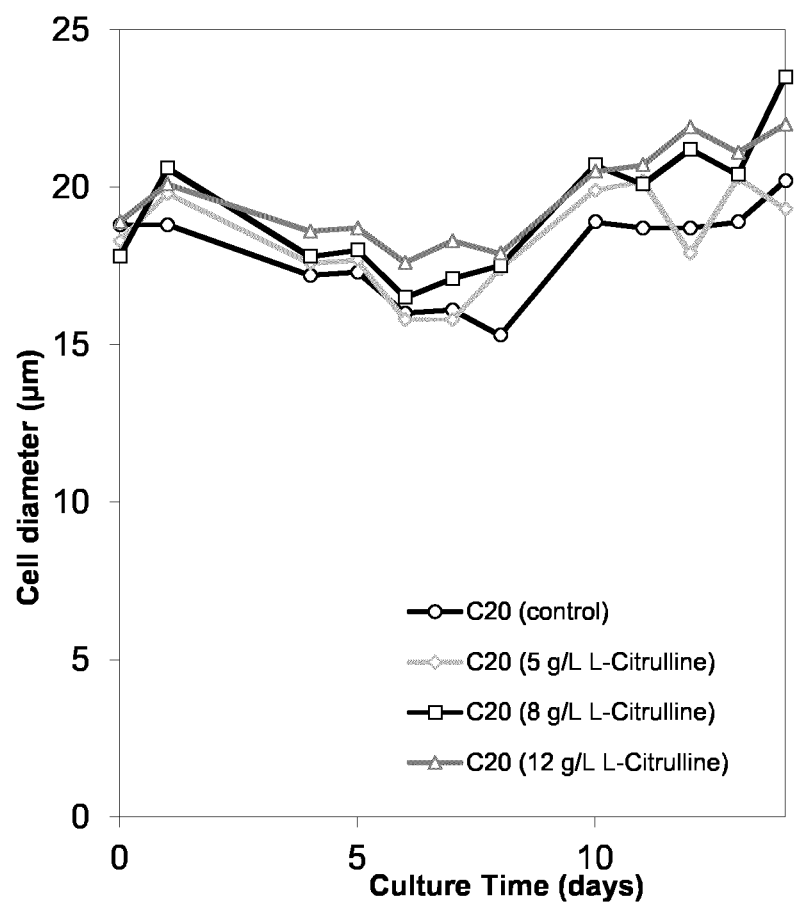
FIG. 2: Cell diameter of CHO cells producing ustekinumab cultured in a cell culture medium containing different concentrations of citrulline or not containing citrulline (control) dependent on the culture time.
Figure 3:
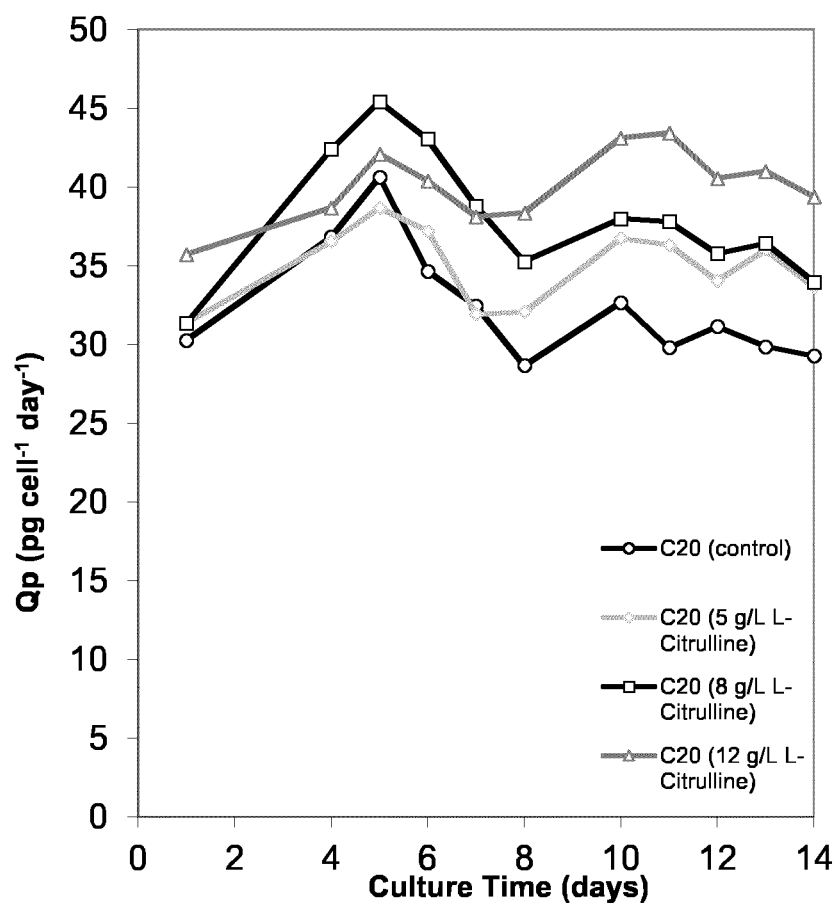
FIG. 3: Specific production rate (Qp) of CHO cells producing ustekinumab cultured in a cell culture medium containing different concentrations of citrulline or not containing citrulline (control) dependent on the culture time.

When adding citrulline, the diameter of the cells expressing ustekinumab surprisingly increases (FIG. 2). In addition, unexpectedly, the specific production rate Qp of the cells for ustekinumab increases (FIG. 3). The same increase in the specific production rate Qp could be observed for cells expressing omalizumab (FIG. 8).

When both citrulline and sucrose are added to the cell culture medium, the diameter of the cells increases in comparison to the diameter of cells cultured only in the presence of citrulline (FIGS. 5a and b) and the specific production rate cells increases in comparison to the specific production rate of cells cultured only in the presence of citrulline (FIGS. 6a and b).

2.3 Analysis of Glycan Composition

Figure 4:
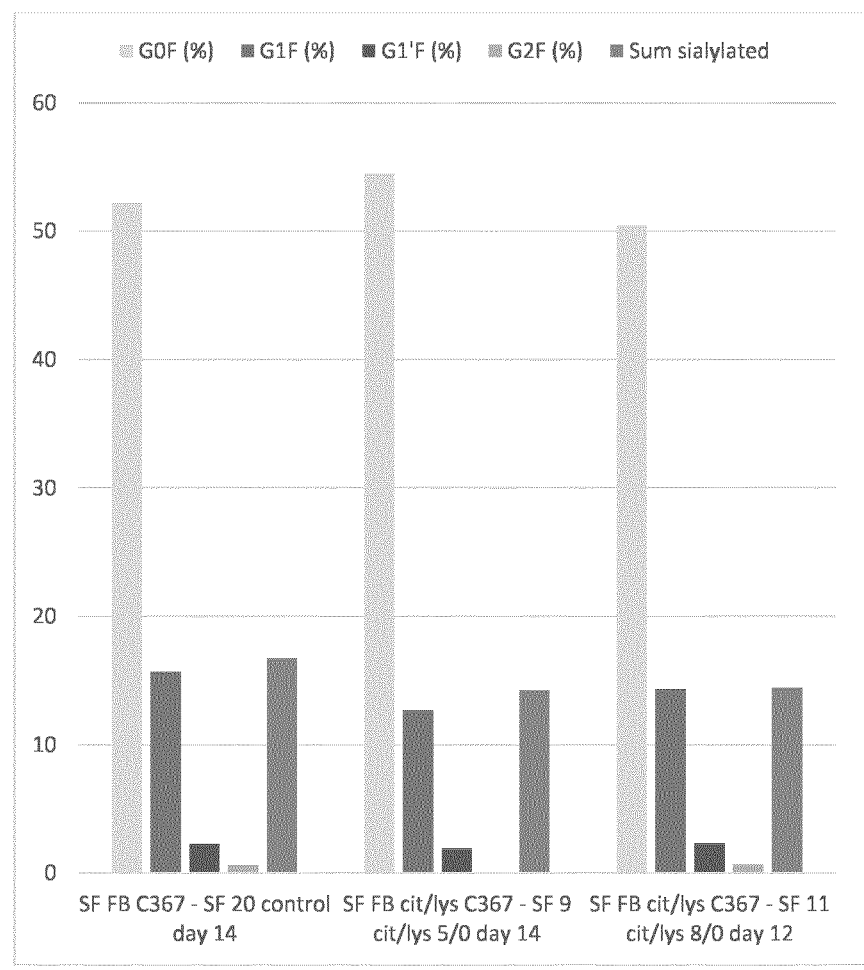
FIG. 4: Analysis of the glycan composition of the ustekinumab antibody produced in CHO cells measured by Rapifluor-MS released N-glycan analysis.

In FIG. 4, the glycan data of the harvests are shown and compared to the control conditions where no citrulline was added to the medium and feed. It can be seen that there are no differences in G0F, G1F, G1'F, G2F and sum of sialylated species when the cells are cultured in a cell culture medium comprising citrulline, showing the specificity of the citrulline effect on acidic and basic species.

2.4 Maximum Depth Filter Capacity and Harvest Quality

The maximum capacity of two depth filters (Merck, D0HC and C0HC) was determined at 1 bar pressure build-up using both a control and a citrulline/sucrose containing cell culture.

FIG. 9 shows that the maximum capacity of both depth filters was increased when a citrulline/sucrose containing cell culture fluid was filtered. C0HC throughput was increased by 42% and D0HC throughput was increased by 39% as compared to control cultures. It should be noted that the capacity increase was not accompanied by an increased filtrate turbidity, which is used as a measure for filtrate quality. C0HC filtrate pools exhibited similar turbidities, e.g.

26.5 and 21.6 FNU for control and citrulline/sucrose containing harvests. Upon D0HC filtration the control pool had a turbidity of 734 FNU and the citrulline/sucrose pool of 320 FNU demonstrating that filter capacity increase is not accompanied by a decrease of filtration quality.

Addition of citrulline and/or sucrose to a cell culture leads to an increased cell specific productivity. Therefore less cell (debris) per gram of product needs to be removed in the subsequent cell clarification step, carried out by depth filtration. Unexpectedly it was observed that the required amount of filter surface per gram of product was decreased during this clarification step as shown by increased filter capacities. The latter provides both economic and technological advantages for the cell culture clarification step.

An increased specific productivity achieved by addition of citrulline and/or sucrose to a cell culture was also shown to yield less cell derived contaminants like host cell-derived proteins (HCPs). HCPs are considered as one of the main contaminants during cell-based production of therapeutic proteins and need to be removed during downstream processing. The lower the initial HCP concentration at harvest, the less needs to be removed in the downstream process. If less cell (mass) is needed to produce a certain amount of product, it is fair to assume that initial product purity is increased in such cultures. The advantages of increased initial product purity for downstream processing are manifold and can range from e.g. lower process development costs to reduction for cost of goods due to higher chromatography resin life-times.

FIG. 10 shows that both filtrate pools of citrulline/sucrose containing cell cultures had lower HCP contaminations per amount of product than the pools from control culture not containing citrulline and sucrose. The observed HCP reduction was 30% for C0HC and 39% for D0HC compared to the control culture.

2.5 Determination of Citrulline Concentrations

Since citrulline is a non-proteingenic amino acid the effects of citrulline may be mediated by citrulline itself or by a potential metabolite of citrulline. It is unknown whether CHO cells can metabolize citrulline. In humans some tissue can metabolize citrulline while other tissues cannot. Since the citrulline concentration added to the culture is identical in medium and feed it can be expected that if CHO cells can metabolize citrulline the concentration during the culture will be lower than the concentration added. However if citrulline is not consumed by the CHO cells, the concentration will not change during the culture period, because the feed contains the identical concentration as was put in the medium.

FIG. 11 shows that the concentration of citrulline during the fermentation does not change significantly, indicating that citrulline is not metabolized by CHO cells. This can only result in the surprising conclusion that the effects of citrulline on acidic and basic variants, cell size and specific productivity are direct effects of citrulline, as this amino acid is not metabolized or build into proteins.

2.6 Determination of Apoptosis and Autophagy

As shown in FIG. 12A, CHO cells treated with 10 g/L L-citrulline/40 mM sucrose for 11 days showed significantly lower caspase 3/7 activity than non-treated control CHO cells. Activation of caspases is a hallmark of programmed cell death or apoptosis. Surprisingly, these results demonstrate that addition of 10 g/L L-citrulline/40 mM sucrose to the cell culture medium reduces caspase 3/7 activity in CHO cells, and therefore seems to trigger anti-apoptotic signals, whereas the specific ustekinumab production rate of these cells was significant increased compared to non-treated control CHO cells (see FIG. 12D).

As shown in FIG. 12B, CHO cells treated with 10 g/L L-citrulline/40 mM sucrose for 11 days showed lower outer membrane phosphatidylserine expression levels than non-treated control CHO cells. Activation of caspase 3 and 7 precedes phosphatidylserine expression from inner to outer cell membrane (Marino et al. (2013) Cell Res 23: 1247-1248). In accordance with above-mentioned lower caspase 3/7 activity in CHO cells cultured in a medium comprising 10 g/L L-citrulline/40 mM sucrose, addition of 10 g/L L-citrulline/40 mM sucrose to the cell culture medium also reduced outer membrane phosphatidylserine expression, again demonstrating the anti-apoptotic action of citrulline and sucrose on CHO cells, whereas the specific ustekinumab production rate of these cells was significant increased compared to non-treated control CHO cells (see FIG. 12D).

As shown in FIG. 12C, CHO cells cultured in a cell culture medium comprising 10 g/L L-citrulline/40 mM sucrose for 11 days showed lower autophagy—characterized by decreased intracellular autophagic vacuole expression levels—than control CHO cells. Autophagy and programmed cell death are intimately linked. For example, both processes often use the same molecular machinery and recent work suggests that autophagy has great influence on a cell's decision to live or die. Considering the above-described effect of culturing in a cell culture medium comprising citrulline and sucrose on the swelling/size and the apoptosis of CHO cells, this culturing affects CHO cells in such a manner that both autophagy and apoptosis are inhibited concomitantly with an increased specific ustekinumab production rate.

The invention claimed is:

1. A method of producing a composition comprising a recombinant antibody in Chinese Hamster Ovary cells expressing said antibody, the method comprising:
    (a) culturing said cells in a cell culture medium comprising 8 to 12 g/l citrulline; and
    (b) obtaining the composition comprising the antibody from the cell culture medium, wherein the composition has a reduced amount of acidic species of the antibody compared to a composition produced by culturing said cells in a cell culture medium not comprising 8 to 12 g/l citrulline.

2. The method according to claim 1, wherein the cell culture medium further comprises 5 to 80 mM sucrose.

3. The method according to claim 1, wherein no additional lysine is added to the cell culture medium.

4. The method according to claim 1, wherein the cells are cultured in fed-batch mode using first a basal medium and then a feed medium.

5. The method according to claim 4, wherein each of the basal medium and the feed medium comprises citrulline.

6. The method according to claim 1, wherein the citrulline is added to the cell culture medium.

7. The method according to claim 1, wherein the temperature is changed from a first temperature to a second temperature during the culturing.

8. The method according to claim 7, wherein the second temperature is from 25° C. to 36° C.

* * * * *